(12) United States Patent
Yadidi et al.

(10) Patent No.: US 10,420,776 B2
(45) Date of Patent: Sep. 24, 2019

(54) ANTIBIOTIC COMPOSITIONS FOR NASAL IRRIGATION AND METHODS

(71) Applicant: RhinoNase, Inc., Beverly Hills, CA (US)

(72) Inventors: Kambiz Yadidi, Los Angeles, CA (US); Amanda Quiroga, Newport (GB); Jagdeep Shur, Santa Monica, CA (US); Jeffrey B. Harris, La Canada, CA (US)

(73) Assignee: RHINONASE, INC., Beverly Hills, CA (US)

( * ) Notice: Subject to any disclaimer, the term of this patent is extended or adjusted under 35 U.S.C. 154(b) by 0 days.

(21) Appl. No.: 15/783,400

(22) Filed: Oct. 13, 2017

(65) Prior Publication Data
US 2018/0104253 A1 Apr. 19, 2018

Related U.S. Application Data

(60) Provisional application No. 62/407,822, filed on Oct. 13, 2016.

(51) Int. Cl.
| *A61K 31/546* | (2006.01) |
| *A61K 9/00* | (2006.01) |
| *A61K 9/16* | (2006.01) |
| *A61K 47/10* | (2017.01) |
| *A61K 47/12* | (2006.01) |
| *A61K 47/32* | (2006.01) |
| *A61K 9/10* | (2006.01) |

(52) U.S. Cl.
CPC .......... *A61K 31/546* (2013.01); *A61K 9/0043* (2013.01); *A61K 9/10* (2013.01); *A61K 9/1617* (2013.01); *A61K 9/1635* (2013.01); *A61K 9/1652* (2013.01); *A61K 47/10* (2013.01); *A61K 47/12* (2013.01); *A61K 47/32* (2013.01)

(58) Field of Classification Search
None
See application file for complete search history.

(56) References Cited

U.S. PATENT DOCUMENTS

| 5,736,151 A | * | 4/1998 | Foster | A61K 9/0019 424/423 |
| 2004/0234457 A1 | * | 11/2004 | Rennie | A01N 43/36 424/46 |
| 2011/0282268 A1 | | 11/2011 | Baker | |
| 2013/0028844 A1 | | 1/2013 | Bilgic | |
| 2014/0371305 A1 | * | 12/2014 | Banov | A61K 47/10 514/460 |
| 2015/0140111 A1 | | 5/2015 | Bilgic | |

FOREIGN PATENT DOCUMENTS

| DE | 202013005992 | | 8/2013 | |
| EP | 0834307 | | 4/1998 | |
| WO | WO 2011094504 A2 | * | 8/2011 | .......... A61M 3/0262 |
| WO | 2012060785 | | 5/2012 | |
| WO | 2013151516 | | 10/2013 | |
| WO | 2018071810 | | 4/2018 | |

OTHER PUBLICATIONS

Uzun et al., "Coprecepitation of Cefuroxime Axetil-PVP composite microparticles by batch supercritical antisolvent process," J. of Supercritical Fluids (2011); 55: pp. 1059-1069.*
Doler, et al., "Comparison of Cefuroxime with or without Intranasal Flucticasone for the Treatment of Rhinosinusitis. The CAFFS Trail: A Randomized Controlled Trial", JAMA, 286(24):3097-105, (Dec. 26, 2001).
United States Patent and Trademark Office, International Search Report and Written Opinion of the International Searching Authpority, dated Feb. 13, 2018 for PCT/US17/56578.

* cited by examiner

*Primary Examiner* — Sreenivasan Padmanabhan
*Assistant Examiner* — Jody L Karol
(74) *Attorney, Agent, or Firm* — FisherBroyles, LLP; James W. Hill

(57) ABSTRACT

Provided herein are pharmaceutical formulations, nasal irrigation fluids, sachets, kits and the like comprising cephalosporin antibiotics, as well as methods of topical treatment of sinusitis and related conditions, methods of delivery of the formulations and fluids to the sinuses, methods of coating the sinuses, and methods of disruption and/or penetration of biofilms in the sinuses.

14 Claims, 4 Drawing Sheets

ANTIBIOTIC COMPOSITIONS FOR NASAL IRRIGATION AND METHODS

This application claims the benefit of U.S. Provisional Application No. 62/407,822, filed Oct. 13, 2016, the disclosure of which is hereby incorporated by reference as if written herein in its entirety.

The present invention relates to compositions and methods for irrigating nasal passages with antibiotic agents, which are useful for treating sinusitis, sinus infections, and related conditions.

BACKGROUND

Sinuses are hollow spaces within the facial bones which are lined with delicate membranes called mucosa, as are the nasal passages, which run from the nostrils to the pharynx. Sinusitis is an inflammation of the mucosa of the sinuses, which can be caused by allergies or infection by viruses, fungi, or bacteria. Rhinitis is inflammation of the mucosa of the nasal passages, and can also have one or more causes. These conditions often occur together as rhinosinusitis.

Symptoms of sinusitis are typically more severe than symptoms of rhinitis. Each of these conditions may be categorized as acute or chronic depending on the duration of the symptoms. Symptoms may include nasal congestion, runny or stuffy nose, white, yellow or green discharge, headache, night time cough, pain in the upper jaw or teeth, fatigue, and fever. More serious infections such as ear infections or meningitis may sometimes follow.

Multiple approaches to treating sinusitis exist, including surgery. Irrigation of the operated or non-operated nasal passages and sinus cavities with a nasal rinse can reduce the symptoms of sinusitis. Nasal rinsing typically uses a saline solution which is dispensed into the nasal passage to clear away allergens, irritants and mucus. This facilitates normal drainage of the sinuses, disrupts microbial growth, and reduces inflammation. Such nasal irrigations with saline solutions have been known and used for years.

Nasal irrigation dispensers for use with saline solutions have been described, as for example in U.S. Pat. No. 5,806,723 ("Device for Lavaging") and U.S. Pat. No. 3,847,145 ("Nasal Irrigation System"), the contents of each of which are hereby incorporated in their entirety. Other disclosed techniques or devices include U.S. Pat. No. 6,520,384 ("Apparatus and method for nasal rinse"), U.S. Pat. No. 6,669,059 ("System and method for passage rinse"), and U.S. Pat. No. 6,540,718 ('Appliance for rinsing"), the contents of each of which are hereby incorporated in their entirety.

A common treatment for sinusitis is the use of antibiotics (antibacterials, antimicrobials), administered orally or intravenously. However, topical application of antibiotics can provide higher concentrations of the drug at the site of the infected sinuses. Topical application can also achieve lower systemic exposure to the antibiotic, potentially reducing side effects associated with a particular agent. The use of nasal nebulizers to provide aerosolized antibiotic agents to the nasal passages has been described, as in U.S. Pat. No. 6,576,224 ("Aerosolized Anti-Infectives, Anti-inflammatories, and Decongestants for the Treatment of Sinusitis"), the contents of which are hereby incorporated in their entirety. Inhalation treatments, however, can be problematic so far as achieving sufficient levels of medicament in the site of infected sinuses.

Nasal irrigation methods using nasal irrigation fluids comprising antibiotic agents, including antibiotic agents, can provide good exposure of the medicament in the infected sinuses while minimizing the irritant effects sometimes associated with aerosolized sprays.

Shapiro et al., WO 2011/094504, describe the topical administration of antibiotic formulations by nasal irrigation. Banov, U.S. Patent Publication No. US 2014/0371305, discloses an antibiotic irrigation composition for the treatment of bacterial infection in the respiratory tract, comprising the antibiotic mupirocin. The contents of these two publications are hereby incorporated into the present application in their entireties.

There remains a need for new nasal irrigation compositions of antibiotic agents that can deliver medicaments in therapeutic concentrations.

SUMMARY

Figure 1:
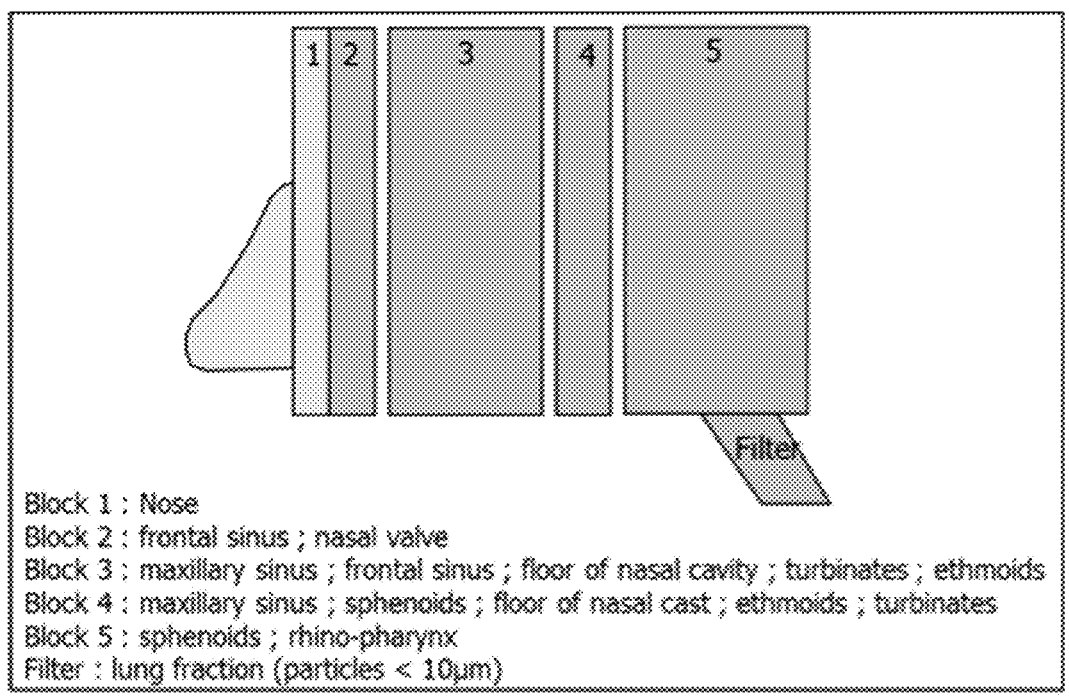
FIG. 1 is a depiction of the nasal cast model used to test Formulations 1-4, with blocks that approximate the regions of the sinuses and other portions of the respiratory passages.

Provided herein are pharmaceutical formulations, nasal irrigation fluids, sachets, kits and the like comprising cephalosporin antibiotics for use in topical treatment of sinusitis and related conditions. Also provided are methods of treatment of, and corresponding uses in treatment of and use of the compositions for the manufacture of a medicament for, sinusitis and related conditions. Also provided are corresponding methods of delivery of the compositions and fluids to the sinuses, for example the maxillary sinus, methods of coating the sinuses, and methods of disruption and/or penetration of biofilms in the sinuses, and corresponding uses.

In certain embodiments, pharmaceutical formulations and nasal irrigation fluids are provided which comprise microparticles comprising an antibiotic agent of the cephalosporin class. The microparticles can be limited to specific size ranges as disclosed herein, and optionally complexed with other agents.

In certain embodiments, the pharmaceutical formulations and nasal irrigation fluids disclosed herein can comprise one or more of a buffering agent, a preservative, a surfactant, a viscosity modifier, an amount of an acid or base sufficient to achieve a target pH, a flow agent, and a molecular inclusion agent.

In certain embodiments, a nasal irrigation fluid is provided which comprises a solution or suspension of an antibiotic agent of the cephalosporin class. In certain embodiments, the nasal irrigation fluid may comprise a suspension of microparticles comprising an antibiotic agent of the cephalosporin class. In certain embodiments, the nasal irrigation fluid may comprise a solution comprising an antibiotic agent of the cephalosporin class. In certain embodiments, the antibiotic agent is cefuroxime. In certain embodiments, the antibiotic agent is cefuroxime axetil. In certain embodiments, the antibiotic agent is cefuroxime sodium.

In certain embodiments, the nasal irrigation fluid comprises a solution or suspension of microparticles of cefuroxime in which cefuroxime is present at a concentration of about 125 mg per 120 mL of fluid, about 750 mg per 120 mL of fluid, about 10 mg per 120 mL of fluid, about 750 mg per 60 mL of fluid, or about 10 mg per 60 mL of fluid. In certain embodiments, the antibiotic agent is cefuroxime axetil. In certain embodiments, the antibiotic agent is cefuroxime sodium. In certain embodiments, the nasal irrigation fluid is a suspension. In certain embodiments, the nasal irrigation fluid is a solution. In certain embodiments, the nasal irrigation fluid comprises a suspension of microparticles of cefuroxime axetil in which cefuroxime is present at a concentration of about 125 mg per 120 mL of fluid.

Also provided is a method for the treatment of sinusitis, the method comprising administering to a nasal passage of a patient in need thereof a nasal irrigation fluid comprising a solution or suspension comprising a cephalosporin antibiotic agent. Also provided is a method for the treatment of sinusitis, the method comprising administering to a nasal passage of a patient in need thereof a nasal irrigation fluid comprising a suspension of microparticles comprising a cephalosporin antibiotic agent. Also provided is a method for the treatment of sinusitis, the method comprising administering to a nasal passage of a patient in need thereof a nasal irrigation fluid comprising a solution comprising a cephalosporin antibiotic agent. In certain embodiments, the antibiotic agent in the nasal irrigation fluid is cefuroxime axetil.

DETAILED DESCRIPTION

Definitions

Unless otherwise defined, all technical and scientific terms used herein have the same meaning as commonly understood by one of ordinary skill in the art of the technical field to which this invention belongs. All publications, patent applications, patents, and other references mentioned herein are incorporated by reference in their entirety. In the case of conflict, the present specification, including definitions, will control. In addition, the materials, methods, and examples are illustrative only not intended to be limiting. Other features and advantages of the invention will be apparent from the following detailed description and claims.

Reference is made throughout this specification to preferred embodiments and specific language will be used to describe the same. The terminology used herein is for the purpose of describing particular embodiments only, and is not intended to limit the scope of the present invention.

As used throughout this disclosure, the singular forms "a," "an," and "the" include plural reference unless the context clearly dictates otherwise. Thus, for example, a reference to "a composition" includes a plurality of such compositions, as well as a single composition, and a reference to "a therapeutic agent" is a reference to one or more therapeutic and/or pharmaceutical agents and equivalents thereof known to those skilled in the art, and so forth. Further, the use of the word "a" or "an" when used in conjunction with the term "comprising the claims and/or the specification may mean" but it s a consistent with the meaning of "one or more," "at least one," and "one or more than one."

Throughout this application, the term "about" is used to indicate that a value includes a variation of ±10% in the stated value.

The term "antibiotic" or, equivalently, "antibiotic agent," or "antimicrobial," refers to an agent that inhibits the growth of or destroys microorganisms, including but not limited to bacteria. An "antibacterial" is an antibiotic that inhibits the growth of or destroys bacteria.

The term "antibiotic agent of the cephalosporin class," or, equivalently, "cephalosporin antibiotic agent" or just "cephalosporin antibiotic," as used herein, refers to an antibiotic that falls within the class of β-lactam antibiotics denoted as cephalosporins as that term is used in the medical literature. Examples of antibiotics of the cephalosporin class are provided herein, and include cefuroxime axetil.

The construction "between X and Y" as used herein, wherein X is a first value and Y is a second value, encompasses the values between these endpoints and the endpoints themselves. As an alternative to this construction, the construction "X-Y" or "from about X to Y" may be used and are intended to be equivalent.

Benzalkonium chloride (BZK) is represented by the following structure:

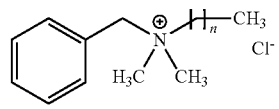

in which n is an integer, and a mixture of more than one thereof can be used. In certain embodiments, n is 8, 10, 12, 14, 16, or 18.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "distilled water," as used herein, generally refers to sterile water that has had most pathogens and impurities and removed by boiling and distillation.

A "nasal irrigation fluid" as used herein refers to an irrigation fluid delivered through the nostril to the nasal passages and/or sinuses of a patient. Nasal irrigation fluids disclosed herein may also be delivered by nebulizers/atomizers.

A "patient," "subject," or "host" to be treated by the methods described herein refers to either a human or non-human animal. Preferred subjects are mammals, including humans, dogs, cats, horses, and livestock.

The term "micronized" refers to a substance that has been subject to a process of micronization. Micronization is the process of reducing the average size of a solid material's particles. Techniques encompassed within the term micronization include milling, grinding, and supercritical fluid processing.

A "microparticle" as used herein refers to a particle, e.g. of a compound or composition, having a diameter of between about 0.1 μm and 100 μm. In certain embodiments, microparticles may have a smaller specified size or size range, for example from 0.1 μm to about 10 μm, less than about 7 μm, from 0.1 μm to about 7 μm, less than about 5 μm, or from 0.1 μm to about 5 μm.

As used herein, two embodiments are "mutually exclusive" when one is defined to be something which is different than the other. For example, an embodiment wherein the amount of cefuroxime axetil in a formulation is specified to be 125 mg is mutually exclusive with an embodiment wherein the amount of cefuroxime axetil is specified to be 10 mg. However, an embodiment wherein the amount of cefuroxime axetil in a formulation is specified to be 125 mg is not mutually exclusive with an embodiment in which a formulation further comprising a viscosity modifier, or in which the pH is between 7.0 and 7.4. Such combinations of embodiments are contemplated here.

When particles are referred to as having a size of a range, e.g., "a diameter between about 0.1 μm and about 10 μm," what is meant is that substantially all particles fall within the range. Because the processes (e.g., micronization, milling, and sieving) typically used to produce particles of a size range are not perfect, it is to be expected and acceptable that a composition (e.g. one which is a powder formulation) may comprise some particles outside the range. In certain embodiments, 80%, 85%, 90%, 95%, 96%, 97%, 98%, 99% or more of the particles will fall within a recited range.

When the symbol "%" (percent) as used herein may mean weight percent (% w/w), volume percent (w/v %), or mole percent, depending on the context in which it is used. When used in reference to a dry pharmaceutical formulation for use in preparation of a nasal irrigation fluid when dissolved or suspended in an aqueous solvent, weight percent is typically meant.

The term "saline," as used herein, means a physiologically acceptable aqueous salt solution, typically sodium chloride (NaCl). Saline may also include phosphate salts.

The term "sinusitis" or, equivalently, "rhinosinusitis," as used herein, means inflammation of the sinuses, usually caused or exacerbated by infection, and includes acute, recurrent acute, subacute, and chronic sinusitis. Symptoms of sinusitis, and related conditions, include: pain and/or pressure, particularly of the facial area and sometimes localized to the affected sinus(es); nasal discharge and post-nasal drip; toothache; headache; fever; and infection of nearby structures such as the eye socket and bone.

The phrase "therapeutically effective" is intended to qualify the amount of active ingredients used in the treatment of a disease or disorder or on the effecting of a clinical endpoint.

As used herein, reference to "treatment" of a patient is intended to include prophylaxis. Treatment may also be preemptive in nature, i.e., it may include prevention of disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

The term "viscosity modifier" as used herein, is intended to be synonymous with "viscosity-enhancing agent."

Compositions

Provided herein are pharmaceutical formulations and nasal irrigation fluids each comprising microparticles comprising an antibiotic agent of the cephalosporin class.

Antibiotics of the cephalosporin class which may be used in any of the compositions and methods disclosed herein include any of the cephalosporins recognized in current practice. Cephalosporins may be further characterized by generation. Non-limiting examples of first-generation cephalosporins include Cefacetrile, Cefadroxil, Cephalexin, Cefaloglycin, Cefalonium, Cefaloridine, Cefalotin, Cefapirin, Cefatrizine, Cefazaflur, Cefazedone, Cefazolin, Cefradine, Cefroxadine and Ceftezole. Non-limiting examples of second generation include Cefaclor, Cefonicid, Cefprozil, Cefuroxime, Cefuzonam, Cefmetazole, Cefotetan, and Cefoxitin. Also included in this category are the following cephems which are sometimes grouped with second generation cephalosporins: Loracarbef, Cefbuperazone, Cefminox, and Cefotiam. Examples of third generation cephalosporins include, without limitation, Cefcapene, Cefdaloxime, Cefdinir, Cefditoren, Cefetamet, Cefixime, Cefmenoxime, Cefodizime, Cefotaxime, Cefovecin, Cefpimizole, Cefpodoxime, Cefteram, Ceftamere, Ceftiofur, Ceftiolene, Ceftizoxime, Ceftriaxone, Cefoperazone, and Ceftazidime. Also included is the cephem Latamoxef which is sometimes grouped with third generation cephalosporins. Non-limiting examples of fourth generation cephalosporins include Cefclidine, Cefepime, Cefluprenam, Cefoselis, Cefozopran, Cefpirome, Cefquinome, and the following cephem which is sometimes grouped with fourth generation cephalosporins: Flomoxef. Non-limiting examples of fifth generation cephalosporins include Ceftobiprole, Ceftaroline, and Cefttolozane. Also included within the scope of cephalosporin antibiotics are cephems which have not yet assigned to a generation, and include without limitation Cefaloram, Cefaparole, Cefcanel, Cefedrolor, Cefempidone, Cefetrizole, Cefvitril, Cefmatilen, Cefemepidium, Cefoxazole, Cefrotril, Cefsumide, Ceftioxide, Cefuracetime, and Nitrocefin.

In certain embodiments, the cephalosporin antibiotic is cefuroxime. In certain embodiments, the cefuroxime is cefuroxime axetil. In certain embodiments, the antibiotic agent is cefuroxime sodium. In certain embodiments, the cephalosporin antibiotic, cefuroxime, cefuroxime sodium, or cefuroxime axetil is complexed with one or more cyclodextrins.

In certain embodiments, the antibiotic agent is micronized to provide the agent as microparticles. In certain embodiments, the microparticles have a diameter of less than about 10 μm. In certain embodiments, the microparticles have a diameter of about 0.1-10 μm. The pharmaceutical formulation or nasal irrigation fluid provided herein is useful for the treatment of sinusitis. In certain embodiments, the microparticles have a diameter less than about 7 μm. In certain embodiments, at least 90% of the microparticles have a diameter of between about 0.75 μm and about 7 μm. In certain embodiments, at least 90% of the microparticles have a diameter of between about 0.75 μm and about 5 μm. In certain embodiments, the microparticles have the following size distribution:

10% of microparticles have a diameter of ≤0.75 μm;
50% of microparticles have a diameter of ≤4.0 μm; and
90% of microparticles have a diameter of ≤5.0 μm.

In certain embodiments, such a microparticle size distribution improves bioavailability and affords prolonged drug activity when delivered as a suspension intranasally, compared to a formulation which has a different microparticle size distribution. In certain embodiments, such a microparticle size distribution improves the length of time that the formulation remains a suspension, i.e., before sedimentation. In certain embodiments, the cephalosporin antibiotic, cefuroxime, cefuroxime sodium, or cefuroxime axetil is complexed with one or more cyclodextrins, and the microparticles therefore comprise cyclodextrin as well.

In certain embodiments, the pharmaceutical formulations and nasal irrigation fluids disclosed herein comprise excipients/carriers in addition to the cephalosporin antibiotic.

In certain embodiments, the pharmaceutical formulation or nasal irrigation fluid further comprises saline.

In certain embodiments, the pharmaceutical formulation or nasal irrigation fluid further comprises a buffering agent. In certain embodiments, the buffering agent is sodium bicarbonate.

In certain embodiments, the pharmaceutical formulation or nasal irrigation fluid further comprises a viscosity modifier. In certain embodiments, the viscosity modifier is chosen from a cellulose polymer, a polyvinylpyrrolidone (povidone, PVP), a polyethylene glycol (PEG), an alginate salt, chitosan, and a polysaccharide (e.g. pectin, tragacanth). In certain embodiments, the viscosity modifier is a cellulose polymer. In certain embodiments, the cellulose polymer is chosen from methylcellulose, carboxymethylcellulose, hydroxyethylcellulose, and hypromellose. In certain embodiments, the PEG is PEG-1000.

In certain embodiments, the pharmaceutical formulation or nasal irrigation fluid further comprises a preservative agent. In certain embodiments, the preservative agent is chosen from benzalkonium chloride, a polyvinylpyrrolidone (povidone), and EDTA.

In certain embodiments, the pharmaceutical formulation or nasal irrigation fluid further comprises a surfactant.

In certain embodiments, the nasal irrigation fluid further comprises a preservative agent. In certain embodiments, the preservative agent is EDTA.

In certain embodiments, the pharmaceutical formulation or nasal irrigation fluid further comprises a surfactant.

In certain embodiments, the antibiotic agent is cefuroxime axetil.

In certain embodiments, the antibiotic agent is cefuroxime sodium.

In certain embodiments, the nasal irrigation fluid comprises a solution or suspension of microparticles of cefuroxime in which cefuroxime is present at a concentration of about 125 mg per 120 mL of fluid, about 750 mg per 120 mL of fluid, about 10 mg per 120 mL of fluid, about 750 mg per 60 mL of fluid, or about 10 mg per 60 mL of fluid. In certain embodiments, the antibiotic agent is cefuroxime axetil. In certain embodiments, the antibiotic agent is cefuroxime sodium. In certain embodiments, the nasal irrigation fluid is a suspension. In certain embodiments, the nasal irrigation fluid is a solution. In certain embodiments, the nasal irrigation fluid comprises a suspension of microparticles of cefuroxime axetil in which cefuroxime is present at a concentration of about 125 mg per 120 mL of fluid.

Tonicity, a measure of the effective osmotic pressure gradient, of the nasal irrigation fluid may be adjusted if needed by tonicity enhancing agents, such as saline. The nasal irrigation fluids of the present invention may be adjusted with tonicity agents to approximate the osmotic pressure of normal lachrymal fluids, which is equivalent to a 0.9% solution of sodium chloride. An osmolality may be of about 225 to 400 mOsm/kg. In some embodiments, an osmolality of 280 to 320 mOsm/kg is achieved. Tonicity enhancing agents suitable for use in the compositions herein include both ionic and non-ionic agents. Ionic tonicity enhancers include without limitation alkali metal or other earth metal halides, such as $CaCl_2$, KBr, KCl, LiCl, NaI, NaBr, and NaCl, as well as $Na_2SO_4$ and boric acid. Non-ionic tonicity enhancing agents include without limitation polyethylene glycol, urea, glycerol, sorbitol, mannitol, propylene glycol, and dextrose.

In certain embodiments, the nasal irrigation fluid is isotonic, hypertonic, or hypotonic. In certain embodiments, the tonicity of the nasal irrigation fluid is that of isotonic saline (0.9% NaCl aqueous solution), or about 300 mOsm/L.

According to certain embodiments, one or more buffers may be added to the compositions to adjust the pH to a desired level. In one embodiment, the pH of the nasal irrigation fluids is about physiological pH. In certain embodiments, the pH of the nasal irrigation is fluid is between about 4.0 and about 9.0, between about 4.0 and about 8.0, between about 3.0 and about 8.0, between about 4.0 and about 6.0, between about 6.5 to about 7.8, or between about 7.1 and about 7.4. In certain embodiments, the pH of the nasal irrigation is fluid is 7.2. In certain embodiments, the pH of the nasal irrigation is fluid is 7.4.

Suitable buffers which may be added to the compositions include buffers such as phosphate, bicarbonate, phthalate, and borate buffers, and by way of non-limiting examples boric acid, sodium borate, potassium citrate, citric acid, sodium bicarbonate, TRIS, and mixed phosphate buffers such as $Na_2HPO_4$, $NaH_2PO_4$, $KH_2PO_4$, and mixtures thereof.

According to certain embodiments, one or more preservatives may be added to the compositions. In certain embodiments, the preservative agent is chosen from a quaternary ammonium compound, a metal chelator, an amino aryl acid ester, an alkyl or aryl alcohol, an alkyl or aryl acid, an alkyl or aryl amide, an organomercurial, a formaldehyde donator, a biguanide, or a phenol. In certain embodiments, the preservative agent is chosen from benzalkonium chloride, benzyl alcohol, a polyvinylpyrrolidone (povidone), and ethylenediaminetetraacetic acid (EDTA, often provided as the disodium salt). In certain embodiments, the preservative is EDTA.

According to certain embodiments, one or more surfactants may be added to the compositions. Surfactants may be anionic, cationic, nonionic, or amphoteric/zwitterionic. Examples of anionic surfactants include, by way of non-limiting example, alkyl sulfates, alkyl ethoxylate sulfates, and soaps such as sodium stearate. Non-limiting examples of cationic surfactants include quaternary ammonium salts such as tetradecyl trimethyl ammonium bromide, benzalkonium chloride, and cetylpyridinium chloride. Non-limiting examples of nonionic surfactants that may be used in the compositions include polysorbates such as polysorbate 20 ("Tween"), Tyloxapol and related 4-(1,1,3,3-tetramethylbutyl)phenol/poly(oxyethylene)polymers, poly(oxyethylene)-poly(oxypropylene) block copolymers, polyethylene glycol esters of fatty acids, such as coconut, polysorbate, polyoxyethylene, polyvinylpyrrolidone (povidone), and polyoxypropylene ethers of higher alkanes ($C_{12}$-$C_{18}$). Examples of amphoteric/zwitterionic surfactants include without limitation alkyl betaines. In certain embodiments, the surfactant is a quaternary ammonium compound. In certain embodiments, the surfactant is benzalkonium chloride.

Compounds disclosed herein as surfactants may act as preservatives, and vice versa. Just two examples are benzalkonium chloride and EDTA.

According to certain embodiments, one or more humectants may be added to the compositions. In certain embodiments, the humectant is chosen from Xylitol, polyethylene glycol (PEG), glycerin, and mannitol. In certain embodiments, the humectant is present in the composition an amount in the range of 0.1-30% w/w.

According to certain embodiments, one or more solubility enhancers may be added to the compositions. In certain embodiments, the solubility enhancer is a cyclodextrin. Cyclodextrins (CDs) are nonreducing, crystalline, water soluble, and cyclic oligosaccharides consisting of glucose monomers arranged in a donut shaped ring having hydrophobic cavity and hydrophilic outer surface. Three naturally occurring CDs are α-Cyclodextrin, β-Cyclodextrin, and γ-Cyclodextrin. The surface of the cyclodextrin molecules makes them water soluble, but the hydrophobic cavity provides a microenvironment for appropriately sized nonpolar molecules. Inclusion complexes incorporating drugs with cyclodextrin to improve solubility may be made by methods known in the art, including kneading, lyophilization, and microwave irradiation. See, e.g., Savjani K T et al., "Drug Solubility: Importance and Enhancement Techniques," ISRN Pharm. 2012: 195727 and Gaurav T et al., "Cyclodextrins in delivery systems: Applications," J Pharm Bioallied Sci. 2010 April-June; 2(2): 72-79. Surfactants can also improve the solubility of a compound. In certain embodiments, cyclodextrins are those which: have minimal local or systemic effect; minimally interfere with the nasal mucociliary functions; show little ciliostatic effect; are non-irritating and non-allergenic; and/or enhance the permeation of drugs across nasal epithelium in a reversible manner. Id.

According to certain embodiments, one or more molecular inclusion agents may be added to the compositions. Such agents permit the formation of a molecular inclusion complex that can aid in slowing or stabilizing the rate of release of a drug from the complex and thereby delivering a drug to the targeted site for a desired period. In certain embodiments, the molecular inclusion agent is a cyclodextrin. Cyclodextrin complexation can also improve the chemical, physical, and thermodynamic stability of a composition, mask odor and taste, and/or enhance bioavailability via improved solubility.

According to certain embodiments, one or more flow agents may be added to the compositions. Examples of flow agents include sugar alcohols such as xylitol and mannitol. Certain flow agents such as xylitol have antibacterial effects as well.

According to certain embodiments, one or more suspending agents/stabilizers may be added to the compositions. Suspending agents include inorganic materials, synthetic compounds, and polysaccharides. Examples of suspending agents include magnesium stearate.

As is well-known in the art, certain excipients disclosed herein can have multiple functions in a formulation. For example, quaternary ammonium compounds such as benzalkonium chloride can function as preservative (even in low amounts), a permeation/penetration enhancer, and/or a cationic surfactant (sometimes at a higher amount for these latter two). As another example, cyclodextrins can act as solubility enhancers and/or molecular inclusion agents for slow release of a compound from an inclusion complex.

According to certain embodiments, the compositions may be subjected to micronization to produce particles within a desired range of particle sizes. Methods for micronization are well known to those skilled in the art of pharmaceutical composition, and include grinding and milling.

Accordingly, one type of formulation provided herein is a nasal irrigation fluid comprising a suspension of microparticles comprising an antibiotic agent of the cephalosporin class. Such nasal irrigation fluids are useful for treating sinusitis and/or related conditions, and symptoms thereof.

In certain embodiments, at least 90% of the microparticles have a diameter of less than about 7 μm.

In certain embodiments, at least 90% of the microparticles of a cephalosporin antibiotic have a diameter between about 0.75 μm and about 7 μm.

In certain embodiments, at least 90% of the microparticles of a cephalosporin antibiotic have a diameter between about 0.75 μm and about 5 μm.

In certain embodiments, the microparticles of a cephalosporin antibiotic have the following size distribution:

10% of microparticles have a diameter of ≤0.75 μm; 50% of microparticles have a diameter of ≤4.0 μm; and 90% of microparticles have a diameter of ≤5.0 μm.

In certain embodiments, the microparticles of a cephalosporin antibiotic are micronized.

In certain embodiments, the cephalosporin antibiotic agent is cefuroxime.

In certain embodiments, the cephalosporin antibiotic agent is cefuroxime axetil.

In certain embodiments, the cephalosporin antibiotic is cefuroxime sodium.

In certain embodiments, the cephalosporin antibiotic, cefuroxime, cefuroxime sodium, or cefuroxime axetil is complexed with one or more cyclodextrins.

In certain embodiments, cefuroxime axetil is present in a dosage of about 50 mg to about 400 mg.

In certain embodiments, cefuroxime axetil is present in a dosage of about 250 mg.

In certain embodiments, cefuroxime axetil is present in a dosage of about 125 mg.

In certain embodiments, the nasal irrigation fluid further comprises sodium chloride.

In certain embodiments, the nasal irrigation fluid further comprises at least one buffering agent(s).

In certain embodiments, the buffering agent is chosen from sodium bicarbonate, sodium citrate, and citric acid.

In certain embodiments, the buffering agent is sodium bicarbonate.

In certain embodiments, the buffering agents are sodium citrate and citric acid.

In certain embodiments, the buffering agent is present in an amount of between 0.001% to 2% (w/w) of the pharmaceutical formulation.

In certain embodiments, the fluid has a pH of about 4.0 to about 9.0.

In certain embodiments, the fluid has a pH of about 3.0 to about 8.0.

In certain embodiments, the fluid has a pH of about 7.0 to about 7.4.

In certain embodiments, the nasal irrigation fluid further comprises a viscosity modifier.

In certain embodiments, the viscosity modifier is a cellulose polymer or polyethylene glycol (PEG).

In certain embodiments, the cellulose polymer is chosen from hydroxyethylcellulose, methylcellulose, hypromellose, and PEG-1000.

In certain embodiments, the nasal irrigation fluid further comprises a preservative or surfactant.

In certain embodiments, the preservative or surfactant is chosen from ethylenediaminetetraacetic acid (EDTA) or a salt thereof, benzalkonium chloride, and polyvinylpyrrolidone (PVP).

In certain embodiments, the nasal irrigation fluid comprises EDTA and benzalkonium chloride as preservative(s) and/or surfactant(s).

In certain embodiments, the nasal irrigation fluid further comprises one or more humectants.

In certain embodiments, the humectant is chosen from Xylitol, polyethylene glycol (PEG), glycerin, and mannitol.

In certain embodiments, the one or more humectant is/are present in the composition an amount in the range of 0.1-30% w/w.

In certain embodiments, cefuroxime axetil is present at a concentration of about 125 mg per 120 mL.

In certain embodiments, the treatment of a condition chosen from acute maxillary sinusitis, acute frontal sinusitis, and acute exacerbation of chronic sinusitis.

Also provided are nasal irrigation fluids formed by the combination of pharmaceutical formulations and the contents of sachets disclosed below with a measured volume of distilled water or other aqueous solution.

In certain embodiments, the measured volume of distilled water is about 20 mL to about 400 mL.

In certain embodiments, the volume is about 100 mL to about 200 mL.

In certain embodiments, the volume is about 100 mL to about 150 mL.

In certain embodiments, the volume is about 120 mL.

In certain embodiments, all excipients are soluble in the aqueous suspension of cephalosporin antibiotic, cefuroxime or cefuroxime axetil.

In certain embodiments, the nasal irrigation fluid has an osmolarity of about 225 mOsm/kg to 400 mOsm/kg.

Also provided are embodiments wherein any embodiment in paragraphs above may be combined with any one or more of these embodiments, provided the combination is not mutually exclusive.

Also provided herein are pharmaceutical formulations, typically in solid powder form for the preparation of a nasal irrigation fluid, comprising:
i. microparticles of a cephalosporin antibiotic;
ii. sodium chloride;
iii. at least one buffering agent;
iv. optionally, at least one preservative or surfactant;
v. optionally, a flow agent;
vi. optionally, a molecular inclusion agent;
vii. optionally, a viscosity modifier;
viii. optionally, a suspending agent; and
ix. an amount of an acid or base sufficient to achieve a pH of between about 3 and about 8 when prepared as a nasal irrigation fluid.

Also provided herein are embodiments wherein any one or more of the optional ingredients in iv.-ix. above are present in the composition.

In certain embodiments, the formulation comprises:
i. microparticles of a cephalosporin antibiotic having a diameter of less than about 7 μm;
ii. sodium chloride;
iii. at least one buffering agent;
iv. a preservative or surfactant; and
v. a viscosity modifier.

In certain embodiments, the formulation comprises:
i. about 10%-about 50% microparticles of a cephalosporin antibiotic having a diameter between about 0.1 μm and about 7 μm;
ii. about 25%-about 90% sodium chloride;
iii. at least one buffering agent, the total amount of buffering agent amounting to about 0.1%-about 2%;
iv. about 0.005% to about 0.05% of a surfactant; and
v. about 0.1% to about 1% of a viscosity modifier.

In certain embodiments, the formulation comprises:
i. about 25% microparticles of a cephalosporin antibiotic having a diameter between about 0.1 μm and about 7 μm;
ii. about 75% sodium chloride;
iii. at least one buffering agent, the total amount of buffering agent amounting to about 0.4%-about 0.5%;
iv. about 0.01% to about 0.05% of a surfactant; and
v. about 0.5% of a viscosity modifier.

In certain embodiments, the buffering agents are a first buffering agent that is an acid, and a second buffering agent that is a salt of the acid.

In certain embodiments, the formulation comprises about 0.2% of the first buffering agent that is an acid, and about 0.28% of the second buffering agent that is a salt of the acid.

In certain embodiments:
the first buffering agent is citric acid or a hydrate thereof;
the first buffering agent is sodium citrate or a hydrate thereof;
the surfactant is chosen from polyvinylpyrrolidone (PVP) and disodium ethylenediaminetetraacetic acid (EDTA); and
the viscosity modifier is polyethylene glycol (PEG) 1000.

In certain embodiments, the surfactant is PVP in an amount of about 0.1%.

In certain embodiments, the surfactant is disodium EDTA in an amount of about 0.5%.

In certain embodiments, the particles of a cephalosporin antibiotic are micronized.

In certain embodiments, the microparticles have a diameter of about 0.1-10 μm.

In certain embodiments, at least 90% of the microparticles have a diameter of less than about 7 μm.

In certain embodiments, at least 90% of the microparticles have a diameter of between about 0.1 μm and about 7 μm.

In certain embodiments, at least 90% of the microparticles of cephalosporin antibiotic have a diameter between about 0.75 μm and about 5 μm.

In certain embodiments, the microparticles of cephalosporin antibiotic have the following size distribution:
10% of microparticles have a diameter of ≤0.75 μm;
50% of microparticles have a diameter of ≤4.0 μm; and
90% of microparticles have a diameter of ≤5.0 μm.

In certain embodiments, the cephalosporin antibiotic is cefuroxime.

In certain embodiments, the cephalosporin antibiotic is cefuroxime axetil.

In certain embodiments, the cephalosporin antibiotic is cefuroxime sodium.

In certain embodiments, the cephalosporin antibiotic, cefuroxime, cefuroxime sodium, or cefuroxime axetil is complexed with one or more cyclodextrins.

In certain embodiments, cefuroxime axetil is present in a dosage of about 50 to about 400 mg.

In certain embodiments, cefuroxime axetil is present in a dosage of about 250 mg.

In certain embodiments, cefuroxime axetil is present in a dosage of about 125 mg.

In certain embodiments, the buffering agent(s) maintains the pH of the formulation in the range of about 3 to about 8.

In certain embodiments, the buffering agent(s) is a weak acid or base.

In certain embodiments, the buffering agent(s) maintains the pH of the formulation in the range of about 7.1 and about 7.4

In certain embodiments, the buffering agent(s) maintains the pH of the formulation in the range of about 7.1 and about 7.2.

In certain embodiments, the buffering agent(s) is present in an amount of between 0.001% to 2% (w/w) of the pharmaceutical formulation.

In certain embodiments, the buffering agent is chosen from sodium bicarbonate, sodium citrate, and citric acid.

In certain embodiments, the buffering agent is sodium bicarbonate.

In certain embodiments, the buffering agent agents are sodium citrate and citric acid.

In certain embodiments, formulation comprises a preservative or surfactant.

In certain embodiments, the preservative or surfactant is chosen from ethylenediaminetetraacetic acid (EDTA) or a salt thereof, benzalkonium chloride, and polyvinylpyrrolidone (PVP).

In certain embodiments, the formulation comprises EDTA and benzalkonium chloride as preservative(s) and/or surfactant(s).

In certain embodiments, the formulation further comprises a viscosity modifier.

In certain embodiments, the viscosity modifier is a cellulose polymer or polyethylene glycol (PEG).

In certain embodiments, the cellulose polymer is chosen from hydroxyethylcellulose, methyl cellulose, hypromellose, and PEG-1000.

In certain embodiments, the formulation comprises one or more humectants.

In certain embodiments, the humectant is chosen from xylitol, polyethylene glycol (PEG), glycerin, and mannitol.

In certain embodiments, the one or more humectants is/are present in the composition an amount in the range of 0.1-30% w/w.

In certain embodiments, the pharmaceutical formulation is chosen from Forms 1-4 as disclosed herein. In certain embodiments, the pharmaceutical formulation is chosen from Form 2 and Form 4. In certain embodiments, the pharmaceutical formulation is Form 1. In certain embodiments, the pharmaceutical formulation is Form 2. In certain embodiments, the pharmaceutical formulation is Form 3. In certain embodiments, the pharmaceutical formulation is Form 4.

Also provided are embodiments wherein any embodiment in paragraphs above may be combined with any one or more of these embodiments, provided the combination is not mutually exclusive.

Also provided is a nasal irrigation fluid comprising:
  i. the pharmaceutical formulation as recited in any embodiment above; and
  ii. a measured volume of distilled water.

In certain embodiments, the measured volume of distilled water is about 20 to about 400 mL.

In certain embodiments, the volume is about 100 to about 200 mL.

In certain embodiments, the volume is about 100 to about 150 mL.

In certain embodiments, the volume is about 120 mL.

In certain embodiments, the nasal irrigation fluid is a solution.

In certain embodiments, the nasal irrigation fluid is a suspension.

In certain embodiments, all excipients are soluble in the aqueous suspension of cephalosporin antibiotic, cefuroxime, or cefuroxime axetil.

Also provided herein is/are one or more packets/sachets each containing a measured volume of an antibiotic composition. In certain embodiments, the antibiotic composition comprises microparticles comprising an antibiotic agent of the cephalosporin class. In certain embodiments, the sachets each comprise microparticles comprising an antibiotic agent of the cephalosporin class, sodium chloride, and a buffering agent. In further embodiments, the sachets additionally comprise a viscosity enhancing agent, such as a cellulose polymer or polyethylene glycol (PEG). In certain embodiments, the antibiotic composition further comprises a preservative. In certain embodiments, the antibiotic composition further comprises a surfactant. In certain embodiments, the antibiotic in the sachet is an antibiotic of the cephalosporin class. In certain embodiments, the antibiotic cephalosporin in the sachets is cefuroxime. In certain embodiments, the antibiotic cephalosporin in the sachets is cefuroxime axetil. In certain embodiments, the antibiotic cephalosporin in the sachets is cefuroxime sodium.

Accordingly, provided herein is a sachet for the preparation of a nasal irrigation fluid, comprising:
  i. a disposable container;
  ii. microparticles of a cephalosporin antibiotic;
  iii. sodium chloride;
  iv. at least one buffering agent;
  v. optionally, at least one preservative or surfactant;
  vi. optionally, a flow agent;
  vii. optionally, a molecular inclusion agent;
  viii. optionally, a viscosity modifier;
  ix. optionally, a suspending agent; and
  x. an amount of an acid or base sufficient to achieve a pH of between about 3 and about 8 when prepared as a nasal irrigation fluid.

Also provided herein are embodiments wherein any one or more of the optional ingredients in v.-x. above are present in the composition.

In certain embodiments, the sachet comprises:
  i. microparticles of a cephalosporin antibiotic having a diameter of less than about 7 µm;
  ii. sodium chloride;
  iii. at least one buffering agent;
  iv. a preservative or surfactant; and
  v. a viscosity modifier.

In certain embodiments, the sachet comprises:
  i. about 10%-about 50% microparticles of a cephalosporin antibiotic having a diameter between about 0.1 µm and about 7 µm;
  ii. about 25%-about 90% sodium chloride;
  iii. at least one buffering agent, the total amount of buffering agent amounting to about 0.1%-about 2%;
  iv. about 0.005% to about 0.05% of a surfactant; and
  v. about 0.1% to about 1% of a viscosity modifier.

In certain embodiments, the sachet comprises:
  i. about 25% microparticles of a cephalosporin antibiotic having a diameter between about 0.1 µm and about 7 µm;
  ii. about 75% sodium chloride;
  iii. at least one buffering agent, the total amount of buffering agent amounting to about 0.4%-about 0.5%;
  iv. about 0.01% to about 0.05% of a surfactant; and
  v. about 0.5% of a viscosity modifier.

In certain embodiments, the buffering agents are a first buffering agent that is an acid, and a second buffering agent that is a salt of the acid.

In certain embodiments, the sachet comprises about 0.2% of the first buffering agent that is an acid, and about 0.28% of the second buffering agent that is a salt of the acid.

In certain embodiments:
  the first buffering agent is citric acid or a hydrate thereof;
  the first buffering agent is sodium citrate or a hydrate thereof;
  the surfactant is chosen from polyvinylpyrrolidone (PVP) and disodium ethylenediaminetetraacetic acid (EDTA); and
  the viscosity modifier is polyethylene glycol (PEG) 1000.

In certain embodiments, the surfactant is PVP in an amount of about 0.1%.

In certain embodiments, the surfactant is disodium EDTA in an amount of about 0.5%.

In certain embodiments, the particles of a cephalosporin antibiotic are micronized.

In certain embodiments, at least 90% of the microparticles have a diameter of less than about 7 µm.

In certain embodiments, at least 90% of the microparticles have a diameter of between about 0.1 µm and about 7 µm.

In certain embodiments, at least 90% of the micronized particles of a cephalosporin antibiotic have a diameter between about 0.75 µm and about 5 µm.

In certain embodiments, the particles of a cephalosporin antibiotic have the following size distribution:

10% of microparticles have a diameter of ≤0.75 µm; 50% of microparticles have a diameter of ≤4.0 µm; and 90% of microparticles have a diameter of ≤5.0 µm.

In certain embodiments, the cephalosporin antibiotic agent is cefuroxime.

In certain embodiments, the cephalosporin antibiotic agent is cefuroxime axetil.

In certain embodiments, the cephalosporin antibiotic agent is cefuroxime sodium.

In certain embodiments, the cephalosporin antibiotic, cefuroxime, cefuroxime sodium, or cefuroxime axetil is complexed with one or more cyclodextrins.

In certain embodiments, cefuroxime axetil is present in a dosage of about 50 to about 400 mg.

In certain embodiments, cefuroxime axetil is present in a dosage of about 250 mg.

In certain embodiments, cefuroxime axetil is present in a dosage of about 125 mg.

In certain embodiments, the buffering agent(s) maintains the pH of the formulation in the range of about 3 to about 8.

In certain embodiments, the buffering agent(s) is a weak acid or base.

In certain embodiments, the buffering agent(s) maintains the pH of the formulation in the range of about 7.1 and about 7.4

In certain embodiments, the buffering agent(s) maintains the pH of the formulation in the range of about 7.1 and about 7.2.

In certain embodiments, the buffering agent is present in an amount of between 0.001% to 2% (w/w) of the pharmaceutical formulation.

In certain embodiments, the buffering agent is chosen from sodium bicarbonate, sodium citrate, and citric acid.

In certain embodiments, the buffering agent is sodium bicarbonate.

In certain embodiments, the buffering agents are sodium citrate and citric acid.

In certain embodiments, the sachet comprises one or more preservatives or surfactants.

In certain embodiments, the preservative or surfactant is EDTA, benzalkonium chloride, and polyvinylpyrrolidone.

In certain embodiments, the sachet comprises EDTA and benzalkonium chloride as preservative(s) and/or surfactant(s).

In certain embodiments, the sachet comprises a viscosity modifier.

In certain embodiments, the viscosity modifier is a cellulose polymer or polyethylene glycol (PEG).

In certain embodiments, the viscosity modifier is chosen from hydroxyethylcellulose, methyl cellulose, hypromellose, and PEG-1000.

In certain embodiments, the sachet additionally comprises one or more humectants.

In certain embodiments, the humectant is chosen from Xylitol, polyethylene glycol (PEG), glycerin, and mannitol.

In certain embodiments, the one or more humectants is/are present in the composition an amount in the range of 0.1-30% w/w.

In certain embodiments, the sachet comprises a pharmaceutical formulation chosen from Forms 1-4 as disclosed herein. In certain embodiments, the pharmaceutical formulation is chosen from Form 2 and Form 4. In certain embodiments, the pharmaceutical formulation is Form 1. In certain embodiments, the pharmaceutical formulation is Form 2. In certain embodiments, the pharmaceutical formulation is Form 3. In certain embodiments, the pharmaceutical formulation is Form 4.

Also provided are embodiments wherein any embodiment above may be combined with any one or more of these embodiments, provided the combination is not mutually exclusive.

Also provided herein is a nasal irrigation fluid comprising a solution or suspension of microparticles comprising an antibiotic agent of the cephalosporin class, which fluid is formed by mixing a pharmaceutical composition as provided herein or the contents of a sachet as provided herein with distilled water or saline solution. In certain embodiments, the formation of the solution or suspension of microparticles of the composition is prepared by combining a measured volume of distilled water with a weighed amount of a pharmaceutical composition as provided herein or the contents of a sachet as provided herein. In certain embodiments, the antibiotic agent is cefuroxime. In certain embodiments, the antibiotic agent is cefuroxime axetil. In certain embodiments, the antibiotic agent is cefuroxime sodium. In certain embodiments, the suspension is prepared in a delivery device as described herein, for example by combining a measured volume of distilled water with a weighed amount of a pharmaceutical composition as provided herein or the contents of a sachet as provided herein in a delivery device such as a nasal irrigation bottle, then agitating the contents, e.g. by shaking or swirling.

Dosages, Volumes, Concentrations, and Administration

The dosage of the antibiotic agent to be delivered via nasal irrigation will vary depending on many factors, including but not limited to the symptoms, the nature and severity of sinusitis to be treated, the age of the patient, and other physical characteristics of the patient, and depending on the pathology of the sinusitis, including the associated pathogen and its features such as film formation and antibiotic resistance.

In certain embodiments, the amount of antibiotic per unit of formulation, sachet, or nasal irrigation fluid to be administered at a time (the dosage) comprises about 50 to about 400 mg of antibiotic per nostril. In certain embodiments, the dosage comprises about 100 to about 200 mg per nostril. In certain embodiments, the dosage comprises about 100 to about 150 mg per nostril. In certain embodiments, the dosage comprises about 125 mg per nostril. In certain embodiments, the dosage is of cefuroxime. In certain embodiments, the dosage is of cefuroxime axetil. In certain embodiments, the dosage is of cefuroxime sodium.

In certain embodiments, the dosages disclosed above and elsewhere herein are delivered to the sinus(es) in a volume of liquid such as a nasal irrigation fluid of about 20 to about 400 mL. In certain embodiments, the volume is about 30 mL to 300 mL. In certain embodiments, the volume is about 100 to about 200 mL. In certain embodiments, the volume is about 100 to about 150 mL. In certain embodiments, the volume is about 120 mL. In any of these embodiments, the liquid may be water (e.g. deionized water), saline, or a buffered solution. In certain embodiments, the volume of nasal irrigation fluid administered to the sinus is per administration per nostril.

In certain embodiments, the antibiotic agent may be present in the nasal irrigation fluid at a concentration of 0.001 mg/mL to 50 mg/mL. In certain embodiments, the antibiotic agent may be present in the nasal irrigation fluid at a concentration of about 0.1 mg/mL to about 10 mg/mL. In certain embodiments, the antibiotic agent may be present in the nasal irrigation fluid at a concentration of about 1 mg/mL to about 5 mg/mL. In certain embodiments, the antibiotic agent may be present in the nasal irrigation fluid at a concentration of about 0.5 mg/mL to about 1.5 mg/mL. In certain embodiments, the antibiotic agent may be present in the nasal irrigation fluid at a concentration of about 1.0 mg/mL to about 1.1 mg/mL. Any concentration between these endpoints is contemplated. The contemplated concentrations of the antibiotic agent in the nasal irrigation fluid include, by way of non-limiting examples, about 0.1 mg/mL, about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, about 0.95 mg/mL, about 0.96 mg/mL, about 0.97 mg/mL, about 0.98 mg/mL, about 1 mg/mL, about 1.01 mg/mL, about 1.02 mg/mL, about 1.03 mg/mL, about 1.04 mg/mL, about 1.05 mg/mL, about 1.1 mg/mL, about 1.2 mg/mL, about 1.3 mg/mL, about 1.4 mg/mL, about 1.5 mg/mL, about 2 mg/mL, about 3 mg/mL, about 4 mg/mL, about 5 mg/mL, about 7 mg/mL, or about 10 mg/mL.

In certain embodiments, the antibiotic agent may be present in the nasal irrigation fluid at a concentration of from about 0.0001% (w/v) to about 5% (w/v). The antibiotic agent may be present from about 0.01% (w/v) to about 3% (w/v). For example, the antibiotic agent may be present from about 0.01% (w/v) to about 1% (w/v). Any concentration between these endpoints is contemplated. The contemplated concentrations of the antibiotic agent in the nasal irrigation fluid include, by way of non-limiting examples, about 0.01% (w/v), about 0.03% (w/v), about 0.05% (w/v), about 0.07% (w/v), about 0.08% (w/v), about 0.09% (w/v), about 0.1% (w/v), about 0.2% (w/v), about 0.3% (w/v), a about 0.4% (w/v), bout 0.5% (w/v), about 0.7% (w/v), about 1% (w/v), about 1.2% (w/v), about 1.4% (w/v), about 1.6% (w/v), about 1.8% (w/v), about 2% (w/v), about 2.2% (w/v), about 2.4% (w/v), about 2.6% (w/v), about 2.8% (w/v), about 3% (w/v), about 3.2% (w/v), about 3.4% (w/v), about 3.6% (w/v), about 3.8% (w/v), about 4% (w/v), about 4.2% (w/v), about 4.4% (w/v), about 4.6% (w/v), about 4.8% (w/v), about 5% (w/v).

In certain embodiments, the dosages, volumes, and concentrations disclosed above and elsewhere herein are administered from one to four times a day, per nostril. In certain embodiments, they are delivered once or twice a day, per nostril. In certain embodiments, they are delivered twice a day, per nostril.

In certain embodiments, the nasal irrigation fluid is administered to each nostril, twice a day. In certain embodiments, administration of the nasal irrigation fluid is performed twice a day daily for 1 to 30 days. In certain embodiments, administration of the nasal irrigation fluid is performed twice a day daily for 7 days. In certain embodiments, administration of the nasal irrigation fluid is performed twice a day daily for 10-14 days. In certain embodiments, administration of the nasal irrigation fluid is performed twice a day daily for 30 days.

In certain embodiments, the dosage comprises 125 mg of cefuroxime axetil in 120 mL of nasal irrigation fluid, delivered per nostril, twice a day.

Also provided are formulation and sachet embodiments wherein any formulation or sachet embodiment above may utilize any of the dosages disclosed herein, as well as nasal irrigation fluid embodiments wherein any nasal irrigation fluid embodiment above above may utilize any of the dosages, volumes, and concentrations disclosed herein, provided the combination is not mutually exclusive.

Delivery Devices

Also provided herein are nasal irrigation delivery devices comprising the formulations and nasal irrigation fluids disclosed herein. Nasal irrigation delivery devices suitable for use may be single-use or multiple-use.

A single-use product may be sterile prior to opening of the package and all the composition in the package is intended to be used in a single application to one or both nasal passages of a subject. The single-dose packaging arrangement may be made by any of known methods. Examples of such packaging methods include blow-filled seals and conventional plastic bottles.

According to certain embodiments, provided herein is a nasal irrigation system or kit comprising an antibiotic composition herein, an applicator or delivery device, and optionally, saline solution. In certain embodiments, the applicator or delivery device includes a structure thereon that adapted for nasal delivery of a nasal irrigation fluid. According to certain embodiments, the delivery device for the nasal irrigation fluid is a positive-pressure squeeze device. Examples of squeeze devices that may be utilized with the nasal irrigation fluids include, without limitation, bottles and bulb syringes.

According to certain embodiments, delivery of the nasal irrigation fluids may use a delivery device to deliver a pressurized stream of nasal irrigation fluid to the nasal passage of a subject. Examples of delivery devices and applicators suitable for use with the compositions herein may be found, for example, in U.S. Pat. No. 5,806,723 ("Device for Lavaging"), U.S. Pat. No. 3,847,145 ("Nasal Irrigation System"), U.S. Pat. No. 6,520,384 ("Apparatus and Method for Nasal Rinse"), U.S. Pat. No. 6,669,059 ("System and Method for Passage Rinse"), U.S. Pat. No. 6,540,718 ("Appliance for Rinsing"), WO 2011/094504 ("Antimicrobial Sinus Irrigation Compositions, Methods, and Devices"), and U.S. Patent Publication No. US 2014/0371305 ("Mupirocin Antibiotic Composition").

According to certain embodiments, the delivery device may be a plastic squeeze bottle that creates a seal to the nostril in order to deliver a stream of nasal irrigation fluid into the sinus passages.

Commercially available examples of suitable nasal irrigation devices include those similar to: the Micfit 250 mL SinuClear Squeeze Bottle (see, e.g., micfit.com/Products/Sinus-Squeeze-Bottle/Sinus-Squeeze-Bottle-250ML.html, accessed on Sep. 27, 2016); the 8 oz NasoPure squeeze bottle (see, e.g., nasopure.com/Nasopure_Nasal_Wash_System_p/sys.htm); the SinuCleanse Squeeze Nasal Wash Bottle (see, e.g., sinucleanse.com/products/sinucleanse-squeeze/), the ActiveSinus Sinus Rinse Bottle (see, e.g, tagaseptic.com/products.html), the NeilMed Sinus Rinse Bottle (see, e.g., shop.neilmed.com/Products/Sinus-Rinse). Children's nasal irrigation devices, which may deliver a smaller volume of fluid, are also contemplated. In some embodiments, the device delivers the nasal irrigation fluid with sufficient pressure to reach and/or coat the sinuses, and in certain embodiments, the deep sinuses specifically; this would be more pressure, for example, than the relatively neutral pressure due to gravity that a neti pot would deliver.

In certain embodiments, the device for delivery of nasal irrigation fluid may be an active sinus device. For example, an electric nasal irrigation device may be used. Such devices are known in the art, and typically comprise a reservoir for holding fluid, a mechanism for delivering fluid, often driven by an electric motor, and at least one nosepiece that conforms to the shape of the nostril. Examples include devices which deliver fluid to the sinuses by gentle ejection, such as the Sinupulse and Hydro Pulse devices (see, e.g., sinupulse.com and hydromed.com) as well as the cordless, handheld Sinugator device from NeilMed (http://shop.neilmed.com/Products/Sinugator-Cordless-Pulsating-Nasal-Wash), and devices which use gentle suction, delivered through two nosepieces, to draw fluid through the sinus passages, such as the Navage device (see navage.com/nose-cleaner-nasal-irrigation-p/bdl-b-nc.htm).

The device for delivery of nasal irrigation fluid may also be a sinus atomizer or nebulizer. Such devices will deliver a mist containing drug to the sinuses. Examples of such devices include those made by Nebology, such as the PARI SINUS Pulsating Aerosol System (see, e.g., nebology.com/pari-sinus-pulsating-aerosol-compressor-system.html).

Additional suitable delivery devices are disclosed in Albu S, "Novel drug-delivery systems for patients with chronic rhinosinusitis," Drug Design, Development and Therapy 2012:6 125-132.

According to certain embodiments the delivery device is filled with a volume of between about 1 mL to about 750 mL of fluid. In certain embodiments, the delivery device is pre-filled with about 1 mL, about 5 mL, 10 mL, about 25 mL, about 50 mL, about 75 mL, about 100 mL, about 125 mL, about 150 mL, about 175 mL, about 200 mL, about 210 mL, about 220 mL, about 240 mL, about 250 mL, about 260 mL, about 270 mL, about 280 mL, about 290 mL, about 300 mL, about 350 mL, or about 400 mL, or a range between any two of these values.

Accordingly, provided herein is a nasal irrigation device comprising a squeeze bottle suitable for nasal irrigation; and either:
 a nasal irrigation fluid as disclosed herein; or
 a nasal irrigation fluid prepared by combining a measured volume of distilled water with the
 pharmaceutical formulation as disclosed herein or the contents of a sachet as disclosed herein.

Also provided herein is a nasal irrigation system comprising an electric nasal irrigation device suitable for nasal irrigation; and either:
 a nasal irrigation fluid as disclosed herein; or
 a nasal irrigation fluid prepared by combining a measured volume of distilled water with the
 pharmaceutical formulation as disclosed herein or the contents of a sachet as disclosed herein.

Also provided herein is a nasal irrigation system comprising a nebulizer or atomizer device suitable for administration of a formulation or fluid as disclosed herein; and either:
 a fluid as disclosed herein; or
 a fluid prepared by combining a measured volume of distilled water with the pharmaceutical formulation as disclosed herein or the contents of a sachet as disclosed herein.

Methods of Treatment and Use

Also provided are methods for the treatment of sinusitis and related conditions. In certain embodiments, the method comprises administering to a nasal passage of a patient in need thereof a nasal irrigation fluid comprising a suspension of microparticles comprising an antibiotic agent. In certain embodiments, the antibiotic agent in the nasal irrigation fluid is a cephalosporin antibiotic. In certain embodiments, the nasal irrigation fluid is a suspension of microparticles of cephalosporin antibiotic. In certain embodiments, the cephalosporin antibiotic in the nasal irrigation fluid is cefuroxime. In certain embodiments, the antibiotic agent in the nasal irrigation fluid is cefuroxime axetil. In certain embodiments, the antibiotic agent in the nasal irrigation fluid is cefuroxime sodium.

In certain embodiments, the volume of nasal irrigation fluid administered to a nasal passage per administration per nostril is between 30 mL and 300 mL. In certain embodiments, the volume of nasal irrigation fluid administered to a nasal passage per administration per nostril is about 120 mL.

In certain embodiments, the nasal irrigation fluid is administered to each nostril, twice a day. In certain embodiments, administration of the nasal irrigation fluid is performed twice a day daily for 1 to 30 days. In certain embodiments, administration of the nasal irrigation fluid is performed twice a day daily for 10-14 days. In certain embodiments, administration of the nasal irrigation fluid is performed twice a day daily for 30 days. In certain embodiments, administration of the nasal irrigation fluid is performed twice a day daily for 7 days.

In certain embodiments, the antibiotic agent is cefuroxime axetil. In certain embodiments, the nasal irrigation fluid comprises cefuroxime present at a concentration of about 125 mg per 120 mL.

In a representative embodiment of a method of use for administering a nasal irrigation fluid, a nasal irrigation fluid comprising a suspension of microparticles comprising an antibiotic agent is present in an appropriate delivery device, such as those described herein. In certain embodiments, the suspension is present in a pre-filled single-use product as described herein. In certain embodiments, the suspension is prepared from a sachet and distilled water or saline as described herein. The user applies the tip of the delivery device snugly against one of the nostril openings. The delivery device is squeezed to force the nasal irrigation fluid to enter the nasal passage. This process is repeated in the other nostril and nasal passage. The nasal irrigation fluid that was injected into the nasal passages should not be swallowed. For single-use product, the device is discarded after use. For multiple-use delivery devices, the device assembly is cleaned after each use.

Conditions to be treated by the methods disclosed herein include: sinus infection, sinusitis, sphenoid sinusitis, rhinitis, rhinosinusitis, nasal allergies, and nasal inflammation, any of which may be acute or chronic. In certain embodiments, the sinusitis (or rhinosinusitis) is chosen from maxillary sinusitis and frontal sinusitis. In certain embodiments, the condition to be treated is acute maxillary sinusitis. In certain embodiments, the condition to be treated is acute frontal sinusitis. In certain embodiments, the condition to be treated is acute exacerbation of chronic sinusitis.

Sinus infection, sinusitis, rhinitis, and rhinosinusitis can be caused by several pathogens. Sixty-six percent of patients with acute sinusitis grow at least 1 pathogenic bacterial species on sinus aspirates, while 26-30% percent of patients have multiple predominant bacterial species. The bacteria most commonly involved in acute sinusitis are part of the normal nasal flora. These bacteria can become sinus pathogens when they are deposited into the sinuses by sneezing, coughing, or direct invasion under conditions that optimize their growth. (See, Brook I et al., "Acute Sinusitis," emedicine.medscape.com/article/232670, updated May 6, 2016, accessed Sep. 27, 2016.)

The most common pathogens isolated from maxillary sinus cultures in patients with acute bacterial rhinosinusitis include *Streptococcus pneumoniae*, *Haemophilus influen-* zae, and *Moraxella catarrhalis. Streptococcus pyogenes, Staphylococcus aureus*, and anaerobes are also associated with acute bacterial rhinosinusitis. Gram-negative organisms, including *Pseudomonas aeruginosa* (15.9%), *Escherichia coli* (7.6%), *Proteus mirabilis* (7.2%), *Klebsiella pneumoniae*, and *Enterobacter* species, predominate in nosocomial sinusitis, accounting for 60% of cases. (Id.) Accordingly, the methods, kits, etc. are useful for the treatment of sinus infection, sinusitis, etc. caused by organisms including *S. pneumonia, H. influenza, M. catarrhalis, S. pyogenes, S. aureus, P. aeruginosa, E. coli, P. mirabilis, K. pneumonia*, and *Enterobacter* species.

Additionally, the development of antibiotic resistance continues to grow as a problem facing patients and clinicians. Accordingly, the US Food and Drug Administration has identified the following pathogens as presenting a potentially serious threat to public health: *Acinetobacter* species, *Aspergillus* species, *Burkholderia cepacia* complex, *Campylobacter* species, *Candida* species, *Clostridium difficile, Coccidioides* species, *Cryptococcus* species, Enterobacteriaceae (e.g., *Klebsiella pneumoniae*), *Enterococcus* species, *Helicobacter pylori, Mycobacterium tuberculosis* complex, *Neisseria gonorrhoeae, N. meningitidis*, non-tuberculous mycobacteria species, *Pseudomonas* species, *Staphylococcus aureus, Streptococcus agalactiae, S. pneumoniae, S. pyogenes*, and *Vibrio cholerae*. The FDA has designated these organisms "qualifying pathogens" for purposes of the Generating Antibiotic Incentives Now (GAIN) Act, intended to encourage development of new antibacterial and antifungal drugs for the treatment of serious or life-threatening infections. The methods, kits, etc. are useful for the treatment of sinus infection, sinusitis, etc. caused by these organisms as well.

Rarely, sinusitis is caused by fungi. Fungal sinusitis (e.g., allergic fungal sinusitis) may appear similar to lower airway disorder and allergic bronchopulmonary aspergillosis. Fungal agents associated with this condition include *Aspergillus* and *Alternaria* species. *Bipolaris* and *Curvularia* species are the most common fungi recovered in allergic fungal sinusitis, accounting for 60% and 20%, respectively, in most studies.

Accordingly, provided herein is a method for the treatment of sinusitis or a related condition, comprising administering to a sinus of a patient in need thereof a nasal irrigation fluid as disclosed herein comprising a therapeutically effective amount of microparticles of a cephalosporin antibiotic agent.

In certain embodiments, the condition is chosen from acute maxillary sinusitis, acute frontal sinusitis, and acute exacerbation of chronic sinusitis.

In certain embodiments, the sinusitis is chronic.

In certain embodiments, the sinusitis is acute.

In certain embodiments, the sinus cavity is the maxillary sinus.

In certain embodiments, the patient has previously had nasal or sinus surgery.

In any of these embodiments, the nasal irrigation fluid may be one as disclosed above.

In certain embodiments, the particles of a cephalosporin antibiotic are micronized.

In certain embodiments, at least 90% of the microparticles have a diameter of less than about 7 μm.

The pharmaceutical formulation as recited in claim #, wherein at least 90% of the microparticles have a diameter of between about 0.1 μm and about 7 μm.

In certain embodiments, at least 90% of the micronized particles of a cephalosporin antibiotic have a diameter between about 0.75 μm and about 5 μm.

In certain embodiments, the particles of a cephalosporin antibiotic have the following size distribution:
  10% of microparticles have a diameter of ≤0.75 μm;
  50% of microparticles have a diameter of ≤4.0 μm; and
  90% of microparticles have a diameter of ≤5.0 μm.

In certain embodiments, the cephalosporin antibiotic agent is cefuroxime.

In certain embodiments, the cephalosporin antibiotic agent is cefuroxime axetil.

In certain embodiments, the cephalosporin antibiotic agent is cefuroxime sodium.

In certain embodiments, the cephalosporin antibiotic, cefuroxime or cefuroxime axetil is complexed with one or more cyclodextrins.

In certain embodiments, cefuroxime axetil is present in a dosage of about 50 to about 400 mg.

In certain embodiments, cefuroxime axetil is present in a dosage of about 250 mg.

In certain embodiments, cefuroxime axetil is present in a dosage of about 125 mg.

In certain embodiments, the volume of the nasal irrigation fluid per administration is about 100 to about 200 mL.

In certain embodiments, the volume of the nasal irrigation fluid per administration is about 100 to about 150 mL.

In certain embodiments, the cefuroxime axetil is present in the nasal irrigation fluid at a concentration of about 125 mg per 120 ml.

In certain embodiments, the nasal irrigation fluid is administered to each nostril, twice a day.

In certain embodiments, administration of the nasal irrigation fluid is performed twice a day daily for 1 to 30 days.

In certain embodiments, administration of the nasal irrigation fluid is performed twice a day daily for 7 days. I
n certain embodiments, administration of the nasal irrigation fluid is performed twice a day daily for 10-14 days.

In certain embodiments, administration of the nasal irrigation fluid is performed twice a day daily for 30 days.

In certain embodiments, the dosage comprises 125 mg of cefuroxime axetil in 120 mL of nasal irrigation fluid, delivered per nostril, twice a day.

In certain embodiments, the nasal irrigation fluid is one as disclosed herein.

In certain embodiments, the method comprises the steps of:
  i. preparing a nasal irrigation fluid by combining a measured volume of distilled water with a weighed amount (a dose) of a composition comprising a cephalosporin antibiotic agent, sodium chloride, an optional viscosity modifier, and a buffering agent and suspending the composition in the distilled water; and
  ii. administering the resulting nasal irrigation fluid by dispensing a measured volume of the nasal irrigation fluid into a nasal passage.

In certain embodiments, the composition is a pharmaceutical formulation, or the contents of a sachet, as disclosed herein.

In certain embodiments, the nasal irrigation fluid has an osmolarity of about 225 to 400 mOsm/kg.

In certain embodiments, the condition is chosen from acute maxillary sinusitis, acute frontal sinusitis, and acute exacerbation of chronic sinusitis.

In certain embodiments, the sinusitis is chronic.

In certain embodiments, the sinusitis is acute.

In certain embodiments, the sinus cavity is the maxillary sinus.

In certain embodiments, the patient has previously had nasal or sinus surgery.

In certain embodiments, cefuroxime axetil is present in a dosage of about 50 to about 400 mg.

In certain embodiments, cefuroxime axetil is present in a dosage of about 250 mg.

In certain embodiments, cefuroxime axetil is present in a dosage of about 125 mg.

In certain embodiments, the volume of the nasal irrigation fluid per administration is about 100 to about 200 mL.

In certain embodiments, the volume of the nasal irrigation fluid per administration is about 100 to about 150 mL.

In certain embodiments, the cefuroxime axetil is present in the nasal irrigation fluid at a concentration of about 125 mg per 120 ml.

In certain embodiments, the nasal irrigation fluid is administered to each nostril, twice a day.

In certain embodiments, administration of the nasal irrigation fluid is performed twice a day daily for 1 to 30 days.

In certain embodiments, administration of the nasal irrigation fluid is performed twice a day daily for 7 days.

In certain embodiments, administration of the nasal irrigation fluid is performed twice a day daily for 10-14 days.

In certain embodiments, administration of the nasal irrigation fluid is performed twice a day daily for 30 days.

In certain embodiments, the dosage comprises 125 mg of cefuroxime axetil in 120 mL of nasal irrigation fluid, delivered per nostril, twice a day.

Also provided is a method for the delivery, to a sinus cavity of a patient with sinusitis or a related condition, of an amount of a cephalosporin antibiotic therapeutically effective to treat the sinusitis or sinus infection, comprising the administration by nasal irrigation of:
  a nasal irrigation fluid as provided herein; or
  a nasal irrigation fluid prepared by combining a measured volume of saline solution with a pharmaceutical formulation or the contents of a sachet as provided herein.

In certain embodiments, the condition is chosen from acute maxillary sinusitis, acute frontal sinusitis, and acute exacerbation of chronic sinusitis.

In certain embodiments, the sinusitis is chronic.

In certain embodiments, the sinusitis is acute.

In certain embodiments, the sinus cavity is the maxillary sinus.

In certain embodiments, the patient has previously had nasal or sinus surgery.

In certain embodiments, cefuroxime axetil is present in a dosage of about 50 to about 400 mg (per unit).

In certain embodiments, cefuroxime axetil is present in a dosage of about 250 mg.

In certain embodiments, cefuroxime axetil is present in a dosage of about 125 mg.

Methods of Sinus Coating

The efficacy of a given topical treatment for sinusitis and related conditions will depend in part on its deposition and/or retention in the sinuses. Certain nasal irrigation fluids disclosed herein are expected not only to reach the sinuses, but to deposit fluid upon the sinuses and coat the sinuses with fluid. Nasal cast models can be used to assess the deposition and coating of fluid on the sinuses.

Accordingly, provided herein is a method of coating the sinus cavity of a patient with sinusitis or a related condition with an amount of a cephalosporin antibiotic therapeutically effective to treat the sinusitis or sinus infection, comprising the administration by nasal irrigation of:
  a nasal irrigation fluid as provided herein; or
  a nasal irrigation fluid prepared by combining a measured volume of saline solution with a pharmaceutical formulation or the contents of a sachet as provided herein.

In certain embodiments, the sinus cavity or cavities is/are chosen from a frontal sinus, maxillary sinus, turbinates, ethmoids, and sphenoids.

In certain embodiments, the sinus cavity is a deep sinus cavity.

In certain embodiments, the sinus cavity is the maxillary sinus.

In certain embodiments, the condition is chosen from acute maxillary sinusitis, acute frontal sinusitis, and acute exacerbation of chronic sinusitis.

In certain embodiments, the patient has previously had nasal or sinus surgery.

In certain embodiments, cefuroxime axetil is present in a dosage of about 50 to about 400 mg (per unit).

In certain embodiments, cefuroxime axetil is present in a dosage of about 250 mg.

In certain embodiments, cefuroxime axetil is present in a dosage of about 125 mg.

Biofilms and Methods of Disruption/Penetration

The management chronic sinusitis (alternatively referred to in the literature as "refractory" or "recalcitrant" sinusitis, particularly when present after sinus surgery) is complex and challenging. It is difficult to determine the underlying etiology of recurrent sinus infections, in part because the presence of biofilms, which can trap and shield bacteria, make identification of the pathogenic organism(s) difficult. A biofilm is an aggregate of cells stuck to each other and/or to a surface, embedded within a matrix of extracellular polymeric substance (EPS, often called a slime). Bacteria can form these biofilms by assembling viable cells together to form a cooperative consortium encased within an exopolysaccharide (or glycocalyx). Biofilms are usually bacterial but in some instances, both bacteria and fungi coexist in biofilms of patients with chronic sinusitis. In infected sinuses, unless the biofilm is shedding sufficient planktonic bacteria that can be cultured, it is possible to miss the real pathogen. The exopolysaccharide formed specializes in attaching to a variety of surfaces. Consequently, the presence of bacterial biofilms at any stage of infection usually results in recurrent bacterial infections due to the ability of dispersed planktonic daughter cells released from bacterial biofilms to colonies new surfaces. More importantly, the biofilm allows bacteria to evade the mucociliary clearance mechanism of the sinuses, and helps them resist conventional oral antibiotics therapies.

Biofilms have been found to be involved in a wide variety of microbial infections in the body, by some estimates, 80% of all infections. Pertinently, biofilms are common in sinusitis; studies have found them to be present on the removed tissue of 80% of patients undergoing surgery for chronic sinusitis. Additionally, sub-therapeutic levels of β-lactam antibiotics induce biofilm formation in bacteria such as *Staphylococcus aureus*, which is known for antibiotic resistance. For all the foregoing reasons, disruption and/or penetration of microbial biofilms can, in certain embodiments, be an important aspect of antibiotic therapy.

Effective biofilm treatment can involve any or all the following: disruption of the biofilm structure, increasing antibiotics penetration and bacterial susceptibility, and interrupting the bacterial quorum sensing signals by which biofilms bacteria interact with neighboring cells. For reasons set forth above, achieving minimally effective antibiotic concentrations inside a biofilm, particularly in sinus tissue, can be difficult with oral antibiotics. A topically applied antibiotic as disclosed herein, optionally together with one or more agents effective to disrupt and/or penetrate the biofilm, would find use in chronic sinusitis.

Agents effective to disrupt and/or penetrate biofilms include, without limitation: surfactants; compounds which control the formation of amyloid-like extracellular fibers, which contribute to the development of biofilm (e.g. benzoquinone derivatives, sesquiterpene lactones, and other compounds known in the art); compounds which inhibit nucleotide signaling, for example compounds which reduce cyclic diguanosine monophosphate (C-di-GMP), which is involved in bacterial transformation from the motile to the sessile state to establish multicellular biofilm communities, and from the virulent state of acute infections to the less virulent but chronic infections; and compounds which inhibit quorum sensing.

In certain embodiments, controlling both infection and inflammation at the mucosal level can be important, as there is an intricate association between infection and inflammation in biofilms. On one hand, bacterial biofilms create and perpetuate the inflammatory reaction that underlies refractory sinusitis. On the other hand, inflammation damages the epithelium, impairs local defenses and subsequently favors bacterial attachment with biofilm formation. Therefore, in addition to eradicating infection, controlling the inflammatory process and/or disrupting or penetrating the biofilm can be an important component of a maximally successful treatment.

Biofilm response to treatment may be assessed by any method known in the art, e.g., with a Colony Forming Units (CFU) assay. In this reliable and quantifiable biofilm assay, sinus mucosal biopsy issue is homogenized and bacterial biofilms are grown on fresh agar plates and then counted, allowing a quantitative assessment of the biofilm response. Alternatively, the patient may report occurrence or recurrence of symptoms.

Accordingly, provided herein is a method of penetration and/or disruption of a bacterial biofilm and treatment of sinusitis or a related condition in a patient in need thereof, comprising administering to a sinus of a patient in need thereof:
a nasal irrigation fluid as disclosed herein; or
a nasal irrigation fluid prepared by combining a measured volume of distilled water with the pharmaceutical formulation as disclosed herein.

Also provided herein is a method of penetration of a bacterial biofilm with an antibiotic and treatment of sinusitis or sinus infection in a patient in need thereof, comprising administering to a sinus of a patient in need thereof:
a nasal irrigation fluid as disclosed herein; or
a nasal irrigation fluid prepared by combining a measured volume of distilled water with a pharmaceutical formulation or the contents of a sachet as disclosed herein.

The methods disclosed above may utilize any of the nasal irrigation fluids disclosed herein, including those formed from pharmaceutical formulations and the contents of sachets as disclosed herein, delivered by the devices as disclosed herein.

Also provided are corresponding second medical uses of—that is, compounds for use in, and use of compounds in the preparation of a medicament for the treatment of—conditions disclosed above.

The invention is further illustrated by the following examples.

Exemplary Formulations

The following table sets forth examples of formulations suitable for combination with distilled water, saline, or another suitable aqueous solvent for preparation of a nasal irrigation fluid. The following examples are unit doses which may be packaged, e.g., in a packet/sachet containing the following fixed amounts of the formulation (optionally, plus or minus amounts permitted in a product approved by a regulatory agency). A single packet or multiple packets may be combined with the water, saline, or other suitable aqueous solvent to form a nasal irrigation fluid.

Ranges of excipients suitable in one type of nasal irrigation fluid include those set forth in Table 1a.

TABLE 1a

| Component | Concentration Range in Nasal Irrigation Fluids |
|---|---|
| Cefuroxime Axetil or Sodium | 0.01-5% w/w |
| Suspending Agent | 0-1% w/w |
| Viscosity Modifier | 0-1% w/w |
| Surfactant | 0-1% w/w |
| Buffer(s) | 0.001-3% w/w |
| Saline/Tonicity Agent | 0.01-5% w/w |
| Flow Agent | 0-1% w/w |
| Molecular Inclusion Agent | 0-1% w/w |
| Humectant | 0-30% w/w |

Ranges of excipients suitable in one type of pharmaceutical formulation for the preparation of a nasal irrigation fluid with distilled water include those set forth in Tables 1b and 1c.

TABLE 1b

| Component | Concentration Range in Pharmaceutical Formulations |
|---|---|
| Cefuroxime Axetil or Sodium | 0.01-99.99% w/w |
| Suspending Agent | 0-5% w/w |
| Viscosity Modifier | 0-5% w/w |
| Surfactant | 0.001-2% w/w |
| Buffer(s) | 0.001-4% w/w |
| Saline/Tonicity Agent | 0.1-90% w/w |
| Flow Agent | 0-1% w/w |
| Molecular Inclusion Agent | 0-1% w/w |
| Humectant | 0-30% w/w |

TABLE 1c

| Component | Additional Concentration Ranges in Pharmaceutical Formulations |
|---|---|
| Cefuroxime Axetil or Sodium | 1-50% w/w |
| Suspending Agent | 0-2% w/w |
| Viscosity Modifier | 0.1-2% w/w |
| Surfactant | 0.005-1% w/w |
| Buffer(s) | 0.01-1% w/w |
| Saline/Tonicity Agent | 10-90% w/w |
| Flow Agent | 0-1% w/w |
| Molecular Inclusion Agent | 0-1% w/w |
| Humectant | 0-10% w/w |

If formulations are prepared with saline solution instead of distilled water, of course, the above ranges may be modified to omit saline/tonicity agents.

The following formulations were prepared by admixture of pre-weighed dry ingredients. Formulations were manufactured using a high-shear Collette mixer. The scale of these formulations was 150 grams. All formulations were prepared as follows.

Micronized cefuroxime axetil and excipients were extruded through a 250 μm sieve mesh. The drug substance, critic acid and sodium citrate were sandwiched between two equal layers of sodium chloride in the MicroGral vessel. The mixer was then operated at 1000 rpm for 2 mins. The blend was allowed to rest in the vessel for 10 mins. Using a spatula, a trough was made into the powder blend and viscosity modifier and surfactant were placed into the trough and the powder removed was placed over the top to cover the materials. The blender was operated at 1000 rpm for 10 mins. The blend was allowed to rest for 30 mins in the vessel. Following this, the formulation was extruded through a 250-μm sieve mesh.

TABLE 2

| Ingredient Class, % (w/w) | Ingredient, % (w/w) | Formulation 1 | 2 | 3 | 4 |
|---|---|---|---|---|---|
| Active Ingredient | Micronized Cefuroxime Axetil | 25% | 25% | 25% | 25% |
| Suspending Agent | Magnesium Stearate | 0.05% | — | — | — |
| Viscosity modifier | PEG 1000 | — | 0.5% | 0.5% | 0.5% |
| Surfactant | Polyvinylpyrrolidone | 0.01% | 0.01% | 0.01% | — |
| Surfactant | Disodium EDTA | — | — | — | 0.05% |
| Buffer | Citric Acid, Monohydrate | 0.2% | 0.2% | 0.2% | 0.2% |
| Buffer | Sodium Citrate, Dihydrate | 0.28% | 0.28% | 0.28% | 0.28% |
| Saline/Flow Agent | Sodium Chloride | 74.5% | 74.01% | 74% | 74% |

Additionally, the following examples can be prepared by admixture of pre-weighed dry ingredients (combined and dispensed from, e.g., a sachet) with deionized water.

TABLES A-F

| | Function | Concentration in Nasal Irrigation Fluid |
|---|---|---|
| Formulation A Component | | |
| Micronized Cefuroxime Axetil | Active Ingredient | 0.1% |
| Magnesium Stearate | Suspending Agent | 0.05% |
| Polyvinylpyrrolidone | Surfactant | 0.01% |
| Citric Acid, Monohydrate | Buffer | 0.20% |
| Sodium Citrate, Dihydrate | Buffer | 0.28% |
| Sodium Chloride | Saline | 0.9% |
| Mannitol | Flow agent | 0.01% |
| Formulation B Component | | |
| Micronized Cefuroxime Axetil | Active Ingredient | 0.1% w/w |
| PEG 1000 | Viscosity modifier | 0.5% w/w |
| Polyvinylpyrrolidone | Surfactant | 0.01% w/w |
| Citric Acid, Monohydrate | Buffer | 0.20% w/w |
| Sodium Citrate, Dihydrate | Buffer | 0.28% w/w |
| Sodium Chloride | Saline | 0.9% w/w |
| Mannitol | Flow agent | 0.4% w/w |
| Formulation C Component | | |
| Micronized Cefuroxime Axetil | Active Ingredient | 0.1% w/w |
| PEG 1000 | Viscosity modifier | 0.5% w/w |

TABLES A-F-continued

| | Function | Concentration in Nasal Irrigation Fluid |
|---|---|---|
| Polyvinylpyrrolidone | Surfactant | 0.01% w/w |
| Citric Acid, Monohydrate | Buffer | 0.20% w/w |
| Sodium Citrate, Dihydrate | Buffer | 0.28% w/w |
| Sodium Chloride | Saline | 0.9% w/w |
| Xylitol | Flow agent/ active | 0.01% w/w |
| Formulation D Component | | |
| Micronized Cefuroxime Axetil | Active Ingredient | 0.1% w/w |
| PEG 1000 | Viscosity modifier | 0.5% w/w |
| Disodium EDTA | Surfactant | 0.05% w/w |
| Citric Acid, Monohydrate | Buffer | 0.20% w/w |
| Sodium Citrate, Dihydrate | Buffer | 0.28% w/w |
| Sodium Chloride | Saline | 0.9% w/w |
| Xylitol | Flow agent/ active | 0.4% w/w |
| Formulation E Component | | |
| Micronized Cefuroxime Axetil | Active Ingredient | 0.1% w/w |
| PEG 1000 | Viscosity modifier | 0.5% w/w |
| Disodium EDTA | Surfactant | 0.05% w/w |
| Citric Acid, Monohydrate | Buffer | 0.20% w/w |
| Sodium Citrate, Dihydrate | Buffer | 0.28% w/w |
| Sodium Chloride | Saline | 0.9% w/w |
| Cyclodextrin | Molecular Inclusion | 0.2% w/w |
| Xylitol | Flow agent/ active | 0.2% w/w |
| Formulation F Component | | |
| Micronized Cefuroxime Axetil | Active Ingredient | 1.2% w/w |
| PEG 1000 | Viscosity modifier | 0.5% w/w |
| Disodium EDTA | Surfactant | 0.05% w/w |
| Citric Acid, Monohydrate | Buffer | 0.20% w/w |
| Sodium Citrate, Dihydrate | Buffer | 0.28% w/w |
| Sodium Chloride | Saline | 0.9% w/w |
| Cyclodextrin | Molecular Inclusion | 0.2% w/w |
| Xylitol | Flow agent/ active | 0.2% w/w |

In certain embodiments are provided specific examples of Formulations A, B, C, D, and E, in which each of the formulation contains the following amount of compound in the following total volume of fluid, together with corresponding amounts of excipients.

TABLE 3

| | Formulation A1, B1, C1, D1, E1 or F1 | Formulation A2, B2, C2, D2, E2 or F2 | Formulation A3, B3, C3, D3, E3, or F3 | Formulation A4, B4, C4, D4, E4, or F4 | Formulation A5, B5, C5, D5, E5, or F5 |
|---|---|---|---|---|---|
| Cefuroxime (mg) | 125 | 750 | 10 | 750 | 10 |
| Total Vol. (mL) | 120 | 120 | 120 | 60 | 60 |
| Conc. (wt/wt %) | 0.10 | 0.62 | 0.01 | 1.22 | 0.02 |

Method of preparation. The foregoing examples may be prepared by methods known in the art. Cefuroxime (axetil or sodium, optionally complexed with cyclodextrin) may be milled to form microparticles of a predetermined size or size range. Alternatively, dry powder cefuroxime (axetil or sodium, optionally complexed with cyclodextrin) may be dispersed with compressed air (3 bar) and sized by laser diffraction (e.g., RODOS dry powder feeder; HELOS laser diffractometer, WINDOX 4.0 software, all Sympatec GmbH, Clausthal-Zellerfeld, Germany).

The cefuroxime may then be blended (using, e.g., a high-shear Colette mixer) with dry excipient ingredient until reasonably homogenous and the resulting formulation apportioned in a pre-weighed amount (e.g., into sachets). These formulations may then be reconstituted with water to form a nasal irrigation fluid. Formulations in which the excipients (with possible exception of the cephalosporin antibiotic) may go completely into solution in the nasal irrigation fluid, instantaneously or in a very short period of time, with minimal mixing or shaking required. Where the nasal irrigation fluid is a suspension, it should have good suspension stability, and in certain embodiments, the suspension should be clear. In certain embodiments, the nasal irrigation fluid will have a pH of 4.

Once prepared, formulations were or may be tested by the methods below.

HPLC/API Identification, Assay & Purity

Formulations 1-4 were tested for drug content and purity. An isocratic HPLC method was adopted to support analysis of drug substance assay and purity. A Waters Symmetry HPLC column was used with a 5 μm particle size. The dimensions of the column were 150 mm×4.6 mm. The column temperature was 40° C. A mobile phase consisting of 38% methanol and 62% water was used. The flow rate of the HPLC pump was 1.0 ml/min and injection volume was 20 μL. The runtime of the method was 24 mins and UV detection was performed at 240 nm. Results are given below in Table 4.

pH

Compositions and fluids disclosed herein are expected to have suitable pH for intranasal administration to the sinuses by irrigation. pH may be assessed by methods known on the art.

Viscosity

Viscosity is a measure of resistance of a fluid to gradual deformation by shear or tensile stress. Higher viscosity fluids are often generally perceived as thicker and more resistant to movement. In traditional IN formulations like Nasonex, a viscosity modifier (typically Avicel, a microcrystalline cellulose) is used to form a thick gel, wherein drug is permanently suspended in an aqueous environment. Such formulations are prepared well in advance of administration and distributed in stable liquid form. However, not all surfactants can be expected to have the eventual, let alone immediate, effect of viscosity modification that an irrigation fluid reconstituted from powder requires. Viscosity of formulations was assessed as set forth below.

Application of Newton's law of viscosity and conservation to the steady flow of a constant density fluid through a straight tube of uniform circular cross section of length L leads to the Hagen-Poiseuille relationship:

$$Q = \frac{\pi(-\Delta\wp)R^4}{8\mu L} \quad (1)$$

where $(-\Delta\wp)$ is the net driving force for the flow, Q is the volumetric flow rate of fluid and R is the tube radius. The quantity $\wp$ is defined as $(p+\rho g h)$ where p is static, or thermodynamic pressure $\rho$ is fluid density, g is the acceleration of gravity and h is the vertical elevation above a datum plane. Thus, $\wp$ represents the combined effects of pressure and gravity in causing the fluid motion.

According to the assumptions of the Hagen-Poiseuille law, the flow must be laminar and free from end effects. If the construction and operation of an experimental apparatus can conform accurately to the key assumptions, it is possible to use Equation (1) to measure the viscosity of Newtonian fluids.

Steady flow Q of a fluid in a long, straight tube that is maintained at a constant temperature and is equipped with a device to measure the pressure gradient $\Delta P/L$ at some distance from the ends of the tube. In most instances, the control of the operating conditions over the entire length of the tube, the cleaning difficulties, and the need for a large sample of liquid to fill the length of the tube prohibit or make very difficult the use of such a device. Other more convenient and compact types of viscometers to which the Hagen-Poiseuille equation may be applied have been developed. The Cannon-Fenske viscometer and other modifications of the Ostwald pipette are examples.

When the total change in the driving force $\wp$ associated with a flow rate Q through a tube is due to hydrostatic head alone, Equation (1) may be written as, $$v = \frac{\pi g(-\Delta h)R^4}{8QL} \quad (2)$$

where $(-\Delta h)$ is upstream elevation minus downstream elevation, called the hydrostatic head difference, and the quantity v is defined as $$v = \mu/\rho \quad (3)$$

and is called the kinematic viscosity.

A commercial Number 200 Cannon-Fenske pipette type viscometer, which is designed for a 20-to-80 centistoke range in kinematic viscosity was used to measure the Kinematic viscosity of the re-constituted formulations.

The viscometer was filled with suspension of re-constituted formulation such that there is an initial elevation difference, or static head $(-\Delta h)$, between the liquid surface in the tube on the right side and that in the spherical bulb at the bottom of the cell. Both surfaces are at atmospheric pressure. Liquid is allowed to drain through the capillary tube, and the efflux time $t_e$ is measured as the time for the liquid level on the right side to drop through the lower bulb. The volume V is the fixed volume contained between the two marks above and below that small reservoir. The elevation difference in Equation (2) is taken to be the average difference between the liquid levels in the larger bulb on the left side, which changes only slightly, and that in the lower bulb on the right as the liquid level drops from the upper mark to the lower one.

Results are shown below in Table 4. Compositions and fluids disclosed herein are expected to have suitable viscosity for coating a sinus cavity. In certain embodiments, coating of the sinus cavity will permit sustained contact between the cephalosporin antibiotic and infected and/or inflamed tissue, prolonging the action of the antibiotic and increasing the effectiveness of the composition.

Blend Homogeneity

Figure 3:
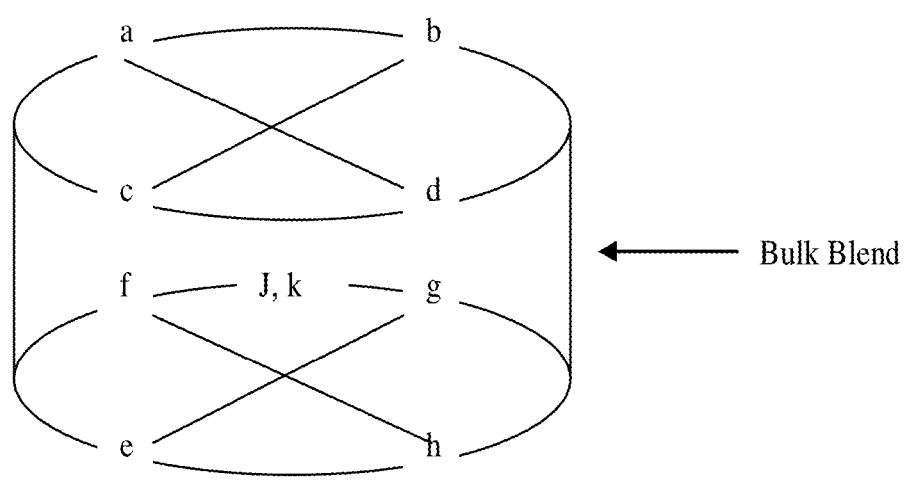
FIG. 3 depicts the sampling location for blend content uniformity of the bulk blend formulation.

Blend content uniformity of Formulations 1-4 was performed by removing of 0.25 g aliquots of powder from 10 equally spaced locations in the formulation bed as shown in FIG. 3. From each of the 10 aliquots, a sub-sample of 15.0±1.0 mg was transferred into a 50 mL volumetric flask.

Approximately 40 mL of diluent was added, and the solution sonicated for 10 minutes to dissolve the powder. The solutions were allowed to return to ambient temperature and then made to volume with diluent solution. These samples were diluted by pipetting 1.0 mL into a 5.0 mL volumetric flask, made up to volume with diluent and shaken to homogenize. One aliquot from each solution was removed and analyzed using HPLC to determine the concentration of Cefuroxime axetil in the solutions.

Per FDA guidance for blended drug powders, blended formulations should be as homogeneous as possible. Percent RSD (relative standard deviation) of all individual results should be 5.0 percent, and within 10.0 percent (absolute) of the mean of the results.

Sedimentation

Physical stability of suspension-based products is also important to maintain dose-to-dose consistency. The sedimentation, flocculation behavior and re-dispersion behavior of a suspension formulation is an interplay between the surface interfacial interactions between drug substance particles in an aqueous suspension, their solubility and density.

Investigation of the sedimentation and flocculation behavior of the drug substance in the aqueous suspension was determined quantitatively using the Turbiscan system (Formulaction, Inc.). This instrument allows characterization of the dispersion state of suspension systems, and provides measurements in terms of size and concentration (such as creaming, sedimentation, flocculation). The physical stability of a suspension based products is important to maintain dose-to-dose consistency. The sedimentation, flocculation behavior and re-dispersion behavior of a suspension formulation is an interplay between the surface interfacial interactions between drug substance particles in an aqueous suspension, their solubility and density.

Figure 4:
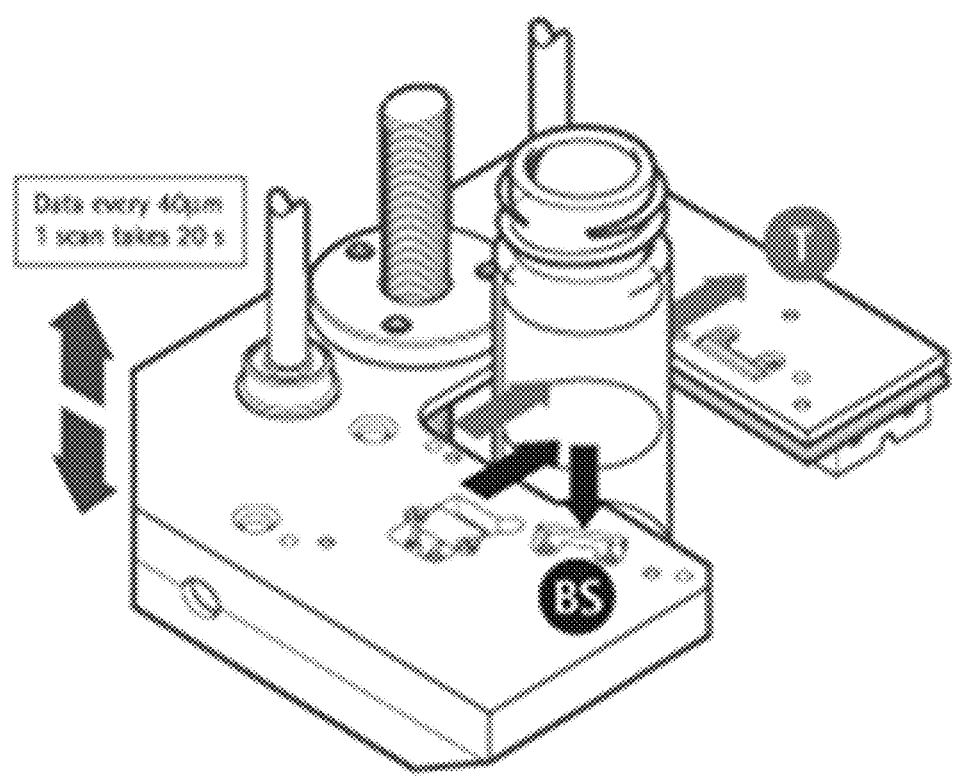
FIG. 4 shows the Turbiscan system used to assess formulation sedimentation.

The Turbiscan system consists of a detection head, which moves up and down along a flat-bottomed cylindrical cell as shown in FIG. 4. The detection head is composed of a pulsed near-infrared light source (L=850 nm) and two synchronous detectors. The transmission detector receives the light, which goes across the sample (at 180° from the incident beam), while the backscattering detector receives the light scattered backward by the sample (at 45° from the incident beam). The detection head scans the entire length of the sample (about 65 mm), acquiring transmission and backscattering data each 40 mm (1625 transmission and backscattering acquisitions per scan). The integrated microprocessor software handles data acquisition, analogue-to-digital conversion, data storage, motor control and computer dialogue.

Results are given below in Table 4.

TABLE 4

| Formulation | Assay (%) | % RSD (BCU) | Viscosity (mPa · S) | pH | Time for Suspension Sedimentation (mins) |
|---|---|---|---|---|---|
| 1 | 91.5 | 16.8 | 0.997 | 6.9 | <0.5 |
| 2 | 98.6 | 2.9 | 0.885 | 7.2 | 2.89 |
| 3 | 89.6 | 22.5 | 0.998 | 6.7 | 1.2 |
| 4 | 99.5 | 3.2 | 0.895 | 7.1 | 3.28 |

As Table 4 above sets forth, Formulations 2 and 4 achieved higher assay percent drug, higher blend homogeneity as evidenced by lower percent RSD, and lower viscosity. Formulations 2 and 4 also had a longer suspension time, which would permit users to mix the drug into an applicator device and have greater confidence that drug would not precipitate out if not used immediately. It is noteworthy that in this instance, lower viscosity was associated with longer sedimentation time.

Stability

Thermodynamic stability of formulations once combined with aqueous solvent may be measured by methods known in the art, for example by standard accelerated conditions involving elevated temperature and humidity over a period of months. Formulations disclosed herein are expected to be thermodynamically stable.

In some embodiments, the nasal irrigation fluid formed by reconstitution of drug-comprising powder in distilled water forms a stable suspension or solution. In certain embodiments, the nasal irrigation fluids disclosed herein will be thermodynamically and/or physically stable for 1, 2, 3, 4, 6, 12, 24, or 48 hours; or four up to 3 or 4 days. In certain embodiments, the nasal irrigation fluids disclosed herein will be stable, once prepared, for at least three hours. In certain embodiments, the nasal irrigation fluids disclosed herein will be stable, once prepared, for at least one hour. In certain embodiments, the nasal irrigation fluids disclosed herein will be stable, once prepared, for at least 24 hours. In certain embodiments, pharmaceutical formulations disclosed herein will be stable for at least one year. In certain embodiments, pharmaceutical formulations disclosed herein will be stable for at least two years.

Formulations 1-4 were tested for stability as dry powders at baseline (ambient conditions, time zero) and following 1-month storage of powders at 40° C. and 75% relative humidity. The chemical stability of the drug substance was measured upon reconstituting the powders in water after 1 hour and after 24 hours. Methods are as disclosed in Ivanovic I et al., "A stability indicating assay method for cefuroxime axetil and its application to analysis of tablets exposed to accelerated stability test conditions," *J. Chromatogr. A* 1119 (2006) 209-215. Results are given below in Table 5.

TABLE 5

| | Assay % for Formulation: | | | | % Impurities for Formulation: | | | |
|---|---|---|---|---|---|---|---|---|
| | 1 | 2 | 3 | 4 | 1 | 2 | 3 | 4 |
| $T_{zero}$-Powder Stability | 91.5 | 98.6 | 98.2 | 99.8 | 5.8 | N.D. | N.D. | N.D. |
| 1M-40/75 Open Dish - Powder Stability | 82.9 | 97.6 | 97.5 | 98.9 | 13.8 | 0.11 | 0.12 | N.D. |
| 1 - Hour Solution Stability | 90.8 | 98.5 | 98.8 | 101.2 | 6.2 | N.D. | N.D. | N.D. |
| 24 - Hour Solution Stability | 89.8 | 98.6 | 98.2 | 99.8 | 7.5 | N.D. | N.D. | N.D. |

As Table 5 above sets forth, Formulations 2 and 4 had superior stability under almost all conditions, and the fewest impurities. In particular, Formulation 4 had very good stability with no detectable impurities at all tested time points.

Efficacy and Safety Assessments

Formulations, nasal irrigation fluids, methods, kits, etc. disclosed herein may be tested in an appropriate assay.

Clinical Trials

Clinical or preclinical trials may be performed in humans and non-human animals to assess efficacy and safety of the formulations, fluids, methods, kits, etc. disclosed herein. Fluids disclosed herein may be administered in a suitable amount comprising a suitable concentration of antibiotic to a suitable number of subjects for a suitable length of time. Symptoms of sinusitis or related condition may be monitored. Adverse effects may also be monitored. Concentration in target tissue (e.g. maxillary sinus) may be assessed either directly (e.g. biopsy or, in animals, post-mortem analysis of histology, bacterial titer, or the like) or by any reasonable technique, such as imaging of labeled drug. Multiple assessments of concentration may be performed to yield pharmacokinetic data as well. Compositions and fluids disclosed herein are expected to be efficacious in these assays.

Nasal Cast Model

Alternatively or additionally, nasal cast models can be used to assess the deposition and coating of fluid on the sinuses. Nasal cast models are useful to measure drug deposition in equivalents of regions of the nasal passages and sinus cavities. See, e.g., Le Guellec S et al., "Validation of anatomical models to study aerosol deposition in human nasal cavities," Pharm Res (2014) 31:228-237.

Formulations 1-4 were tested in a nasal cast model of drug deposition, as depicted in FIG. 1. The nasal cast used was separated into the following anatomical regions—nose, nasal valve, frontal sinus, floor of cavity, turbinates, maxillary sinus, olfactive region, sphenoids, rhinopharynx. Prior to testing, 1 g of powder formulation was weighed into a plastic bottle and reconstituted in 240 mL of double distilled water. An applicator was used to dose the formulation into the cast by positive pressure applied by the analyst. A complete dose was applied to the nasal cast using the following parameters were used: no airflow, device angle of delivery ~60° (from horizontal), one dose in each nostril. Samples from the nasal cast were collected and analyzed using the HPLC method.

Figure 2:
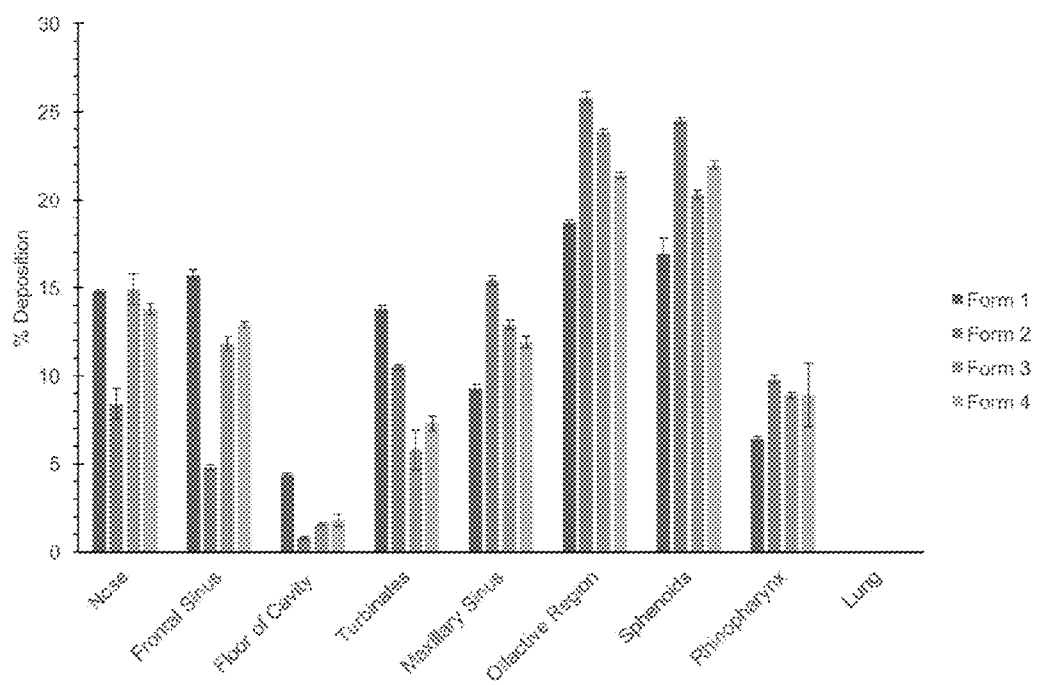
FIG. 2 is a graph depicting the results of assessment of Formulations 1-4 in the nasal cast model.

Results are shown in FIG. 2 and as set forth in Table 6 below.

maxillary sinus, and to provide adequate dwell time in the sinus to treat disease. Additional nasal cast models are described in Le Guellec S et al, "Validation of Anatomical Models to Study Aerosol Deposition in Human Nasal Cavities," Pharm Res (2014) 31(1): 228-37; R Hughes et al., "Development of a nasal cast model to test medicinal nasal devices," Proc Inst Mech Eng, Part H: Journal of Engineering in Medicine, (2008) 222: 1013-22.

Alternatively or additionally, the efficacy of the formulations and nasal irrigation fluids disclosed herein may be assessed in an appropriate in vitro model. For example, in one in vitro model of the nasal epithelia, cultures of bacteria (optionally biofilms) are submerged in a formulation/fluid and the rate of absorption and killing of the bacteria is evaluated Compositions and fluids disclosed herein are expected to effectively kill bacteria.

Biofilm Formation/Penetration Assays

Biofilm Formation.

Biofilms of bacteria of interest may be cultured by methods known in the art. For example, E coli NCTC 10148 may be grown overnight in Luria-Bertani (LB) broth before the density is adjusted to a 0.5 McFarland standard and applied to MHA plates to enable the growth of a confluent lawn. The NCTC biofilm is often used in these studies since it is an established model, and its structure and maturation are well understood. Alternatively, for example, biofilms of P. aeruginosa may be prepared according to a method adapted from Anderl et al. (2000). Briefly, cultures of P. aeruginosa are grown overnight at 37° C. in casamino acid media supplemented with magnesium chloride. The bacterial culture is diluted to give ca. 106 cfu/mL and 5 mL of this diluted inoculum is used to seed a UV-sterilized 13 mm diameter, 0.2 m pore size polycarbonate nucleopore membrane (Whatman). Membranes are placed on Mueller-Hinton agar (MHA) plates and incubated for 24 h at 37° C. after which time they are transferred onto fresh MHA for a further 24 h. See, e.g., Marshall L J at al., "Investigation of the enhanced antimicrobial activity of combination dry powder inhaler formulations of lactoferrin," Int J Pharm. 2016 Sep. 11.

TABLE 6

|  | Form 1 | SD | Form 2 | SD | Form 3 | SD | Form 4 | SD |
| --- | --- | --- | --- | --- | --- | --- | --- | --- |
| Nose | 14.8 | 0.11 | 8.4 | 0.9 | 14.9 | 0.89 | 13.8 | 0.32 |
| Frontal Sinus | 15.7 | 0.32 | 4.8 | 0.14 | 11.8 | 0.42 | 12.9 | 0.17 |
| Floor of Cavity | 4.4 | 0.08 | 0.8 | 0.08 | 1.6 | 0.08 | 1.8 | 0.33 |
| Turbinates | 13.8 | 0.19 | 10.5 | 0.15 | 5.8 | 1.12 | 7.3 | 0.42 |
| Maxillary Sinus | 9.3 | 0.23 | 15.4 | 0.29 | 12.9 | 0.24 | 11.9 | 0.33 |
| Olfactive Region | 18.7 | 0.19 | 25.8 | 0.34 | 23.8 | 0.19 | 21.4 | 0.16 |
| Sphenoids | 16.9 | 0.9 | 24.5 | 0.19 | 20.3 | 0.22 | 22 | 0.23 |
| Rhinopharynx | 6.4 | 0.15 | 9.8 | 0.22 | 8.9 | 0.15 | 8.9 | 1.8 |
| Lung | 0 | 0.003 | 0 | 0 | 0.01 | 0 | 0 | 0 |

As FIG. 2 and Table 6 show, formulations 1-4 do reach the deep sinus passages, with Formulations 2-4 being better than Formulation 1 at reaching regions equivalent to deep sinus structures such as maxillary sinus, olfactive region, sphenoids, etc. Good delivery of the therapeutic agent to the olfactory regions and lower was demonstrated, which is important because much of the inflammation associated with CRS occurs in this region, and currently standard nasal sprays cannot reach this area of the intranasal cavity effectively.

Compositions and fluids disclosed herein are expected to reach, deposit in, and coat the sinus cavities, for example the Crystal violet staining may be used to assess the effects of compounds on biofilm formation. Overnight cultures are diluted 1:100 (v/v) into fresh medium supplemented with magnesium chloride, glucose and casamino acids. To examine the effects of compounds on biofilm formation, aliquots are dispensed into a 96 well plate in the presence of the compounds (e.g., at 2 mg/ml). Plates are incubated at 37° C. for 24 h, after which time excess broth is removed and the biofilm is stained with crystal violet. To examine the effects of the compounds on a pre-formed biofilm, overnight cultures, diluted 1:100 as above, are incubated at 37 C° for 24 h before compounds are added and plates incubated for a further 24 h prior to biofilm staining. In both cases, following the appropriate incubation times, the adherent biofilm is washed twice with distilled water before staining with 0.1% (w/v) crystal violet in distilled water for 15 min at room temperature. Following vigorous washing with water, the crystal violet-stained biofilms are solubilized in 30% (v/v) acetic acid and the absorbance at 550 nm may be determined by plate reader (Multiskan Spectrum, Thermo Fisher Scientific Oy, Vantaa, Finland) using 30% v/v acetic acid in water as the blank. Id.

The biofilm penetration of compounds of interest may be determined using a method modified from Singh et al. (2010). Briefly, the membranes supporting biofilm growth are transferred to MHA plates inoculated with bacteria, e.g., *E. coli*. A UV-sterilized 6 mm diameter, 0.2 m pore size nucleopore polycarbonate membrane (Whatman) is placed on top of each biofilm together with the antibiotic disc, containing the compounds of interest. All plates are incubated at 37° C. for 24 h before the diameters of the clear zones of inhibition of growth were measured. Controls comprising membranes and antibiotic discs without biofilms and biofilms with "empty" discs are also set up. Id.

Antibiotic discs containing one or more cefuroxime antibiotics with the different preparations of lactoferrin may be prepared locally. Antibiotic discs are applied to the agar following inoculation with *E coli* and plates are incubated for 24 h at 37° C. Zones of inhibition are measured after this incubation period and used to construct a calibration curve for antibiotic effects. A calibration plot of the diameter of the zone of inhibition against log concentration (for antibiotic discs containing 1-10,000 mg) is used to determine the concentration of the antibiotic in the combination discs that passes through the biofilms. The diameter of the zones of inhibition in the controls (no biofilm) are taken to signify 100% penetration and used to determine the percent penetration of the antibiotics through the biofilms. All experiments are performed in triplicates and a two-tailed, paired t-test is used for statistical analysis. To avoid false negative results arising from side diffusion from the antibiotic disc around the biofilm, rather than through the biofilm, only biofilms <13 mm in diameter are used in this assay. Id.

The methods above may be modified to assess topical treatment with a formulation that would be suitable for use in a nasal irrigation fluid. Dry formulations could be pressed into discs such as those disclosed above, with modifications suitable to the experiment. Or, for example, instead of using antibiotic discs disclosed above, membranes or other structures supporting biofilms could be sprayed, rinsed, or washed with fluids as disclosed herein. Alternatively, fluid-eluting reservoirs containing fluids as disclosed herein could be placed onto agar plates inoculated with the biofilm-forming bacteria of interest.

Compositions and fluids disclosed herein are expected to penetrate and disrupt biofilms, allowing better treatment of disease.

Kits

Also provided herein are kits for the treatment of sinusitis and related conditions by nasal irrigation. In certain embodiments, the kit comprises:
i. a squeeze bottle suitable for nasal irrigation;
ii. a pharmaceutical formulation disclosed herein or a sachet as disclosed herein; and
iii. instructions for preparing a nasal irrigation fluid by combining a measured volume of distilled water with the pharmaceutical formulation disclosed herein or the contents of a sachet as disclosed herein; and
iv. instructions for administering the nasal irrigation fluid to a sinus cavity.

OTHER EMBODIMENTS

The present disclosure further provides the following non-limiting embodiments.
1. A nasal irrigation fluid for treating sinusitis or a related condition, comprising a suspension of microparticles comprising a cephalosporin antibiotic.
2. The nasal irrigation fluid as recited in embodiment 1, wherein at least 90% of the microparticles have a diameter of less than about 7 μm.
3. The nasal irrigation fluid as recited in embodiment 2, wherein at least 90% of the microparticles of a cephalosporin antibiotic have a diameter between about 0.75 μm and about 7 μm.
4. The nasal irrigation fluid as recited in embodiment 3, wherein at least 90% of the microparticles of a cephalosporin antibiotic have a diameter between about 0.75 μm and about 5 μm.
5. The nasal irrigation fluid as recited in embodiment 4, wherein the microparticles of a cephalosporin antibiotic have the following size distribution:
10% of microparticles have a diameter of ≤0.75 μm;
50% of microparticles have a diameter of ≤4.0 μm; and
90% of microparticles have a diameter of ≤5.0 μm.
6. The nasal irrigation fluid as recited in any of embodiments 1-5, wherein the cephalosporin antibiotic agent is cefuroxime.
7. The nasal irrigation fluid as recited in embodiment 6, wherein the cephalosporin antibiotic agent is cefuroxime axetil.
8. The nasal irrigation fluid as recited in any of embodiments 1-6, further comprising sodium chloride.
9. The nasal irrigation fluid as recited in any of embodiments 1-7, further comprising at least one buffering agent.
10. The nasal irrigation fluid as recited in embodiment 9, wherein the at least one buffering agent(s) is/are chosen from sodium bicarbonate, sodium citrate, and citric acid.
11. The nasal irrigation fluid as recited in embodiment 9, wherein the buffering agents are sodium citrate and citric acid.
12. The nasal irrigation fluid as recited in any of embodiments 1-11, wherein the buffering agent is present in an amount of between 0.001% to 2% (w/w) of the pharmaceutical formulation.
13. The nasal irrigation fluid as recited in any of embodiments 1-12, wherein the fluid has a pH of about 7.0 to about 7.4.
14. The nasal irrigation fluid as recited in any of embodiments 1-13, further comprising a viscosity modifier.
15. The nasal irrigation fluid as recited in embodiment 14, wherein the viscosity modifier is a cellulose polymer or polyethylene glycol (PEG).
16. The nasal irrigation fluid as recited in embodiment 15, wherein the viscosity modifier is chosen from hydroxyethylcellulose, methylcellulose, hypromellose, and PEG-1000.
17. The nasal irrigation fluid as recited in any of embodiments 1-16, further comprising a preservative or surfactant.
18. The nasal irrigation fluid as recited in embodiment 17, wherein the preservative or surfactant is chosen from ethylenediaminetetraacetic acid (EDTA) or a salt thereof, benzalkonium chloride, and polyvinylpyrrolidone (PVP).

19. The nasal irrigation fluid as recited in any of embodiments 1-18, wherein the microparticles of a cephalosporin antibiotic are micronized.
20. The nasal irrigation fluid as recited in any of embodiments 1-19, wherein cefuroxime axetil is present in a dosage of about 50 to about 400 mg.
21. The nasal irrigation fluid as recited in embodiment 20, wherein cefuroxime axetil is present in a dosage of about 250 mg.
22. The nasal irrigation fluid as recited in embodiment 20, wherein cefuroxime axetil is present in a dosage of about 125 mg.
23. The nasal irrigation fluid as recited in any of embodiments 1-22, wherein cefuroxime axetil is present at a concentration of about 0.5 mg/mL to about 1.5 mg/mL.
24. The nasal irrigation fluid as recited in any of embodiments 1-22, wherein cefuroxime axetil is present at a concentration of about 125 mg per 120 mL.
25. A pharmaceutical formulation in solid powder form for the preparation of a nasal irrigation fluid, comprising:
   i. microparticles of a cephalosporin antibiotic having a diameter less than about 7 μm;
   ii. sodium chloride;
   iii. at least one buffering agent;
   iv. optionally, at least one preservative or surfactant;
   v. optionally, a flow agent;
   vi. optionally, a molecular inclusion agent;
   vii. optionally, a viscosity modifier;
   viii. optionally, a suspending agent; and
   ix. an amount of an acid or base sufficient to achieve a pH of between about 3 and about 8 when prepared as a nasal irrigation fluid.
26. The pharmaceutical formulation as recited in embodiment 25, comprising:
   i. microparticles of a cephalosporin antibiotic having a diameter between about 0.1 and about 7 μm;
   ii. sodium chloride;
   iii. at least one buffering agent;
   iv. a preservative or surfactant; and
   v. a viscosity modifier.
27. The pharmaceutical formulation as recited in embodiment 26, comprising:
   i. about 10%-about 50% microparticles of a cephalosporin antibiotic having a diameter between about 0.1 μm and about 7 μm;
   ii. about 25%-about 90% sodium chloride;
   iii. at least one buffering agent, the total amount of buffering agent amounting to about 0.1%-about 2%;
   iv. about 0.005% to about 0.05% of a surfactant; and
   v. about 0.1% to about 1% of a viscosity modifier.
28. The pharmaceutical formulation as recited in embodiment 27, comprising:
   i. about 25% microparticles of a cephalosporin antibiotic having a diameter between about 0.1 μm and about 10 μm;
   ii. about 75% sodium chloride;
   iii. at least one buffering agent, the total amount of buffering agent amounting to about 0.4%-about 0.5%;
   iv. about 0.01% to about 0.05% of a surfactant; and
   v. about 0.5% of a viscosity modifier.
29. The pharmaceutical formulation as recited in embodiment 28, wherein the buffering agents are a first buffering agent that is an acid, and a second buffering agent that is a salt of the acid.
30. The pharmaceutical formulation as recited in embodiment 29, wherein the formulation comprises about 0.2% of the first buffering agent that is an acid, and about 0.28% of the second buffering agent that is a salt of the acid.
31. The pharmaceutical formulation as recited in any of embodiments 25-30, wherein:
   the first buffering agent is citric acid or a hydrate thereof;
   the first buffering agent is sodium citrate or a hydrate thereof;
   the surfactant is chosen from polyvinylpyrrolidone (PVP) and disodium ethylenediaminetetraacetic acid (EDTA); and
   the viscosity modifier is polyethylene glycol (PEG) 1000.
32. The pharmaceutical formulation as recited in embodiment 31, wherein the surfactant is PVP in an amount of about 0.1%.
33. The pharmaceutical formulation as recited in embodiment 32, wherein the surfactant is disodium EDTA in an amount of about 0.5%.
34. The pharmaceutical formulation as recited in any of embodiments 25-33, wherein the particles of a cephalosporin antibiotic are micronized.
35. The pharmaceutical formulation as recited in embodiment 34, wherein at least 90% of the microparticles have a diameter of less than about 7 μm.
36. The pharmaceutical formulation as recited in embodiment 35, wherein at least 90% of the microparticles have a diameter of between about 0.1 μm and about 7 μm.
37. The pharmaceutical formulation as recited in any of embodiments 25-36, wherein at least 90% of the microparticles of a cephalosporin antibiotic have a diameter between about 0.75 μm and about 5 μm.
38. The pharmaceutical formulation as recited in embodiment 37, wherein the particles of a cephalosporin antibiotic have the following size distribution:
   10% of microparticles have a diameter of ≤0.75 μm;
   50% of microparticles have a diameter of ≤4.0 μm; and
   90% of microparticles have a diameter of ≤5.0 μm.
39. The pharmaceutical formulation as recited in any of embodiments 25-38, wherein the cephalosporin antibiotic is cefuroxime.
40. The pharmaceutical formulation as recited in embodiment 39, wherein the cephalosporin antibiotic is cefuroxime axetil.
41. The pharmaceutical formulation as recited in any of embodiments 25-40, wherein cefuroxime axetil is present in a dosage of about 50 to about 400 mg.
42. The pharmaceutical formulation as recited in embodiment 41, wherein cefuroxime axetil is present in a dosage of about 250 mg.
43. The pharmaceutical formulation as recited in embodiment 41, wherein cefuroxime axetil is present in a dosage of about 125 mg.
44. The pharmaceutical formulation as recited in any of embodiments 25-42, wherein the buffering agent is a weak acid or base.
45. The pharmaceutical formulation as recited in embodiment 44, wherein the buffering agent maintains the pH of the formulation in the range of about 7.0 and about 7.4
46. The pharmaceutical formulation as recited in embodiment 45, wherein the buffering agent maintains the pH of the formulation in the range of about 7.1 and about 7.2
47. The pharmaceutical formulation as recited in any of embodiments 25-46, wherein the buffering agent(s) are chosen from sodium bicarbonate, sodium citrate, and citric acid.

48. The pharmaceutical formulation as recited in embodiment 47, wherein the buffering agent agents are sodium citrate and citric acid.
49. The pharmaceutical formulation as recited in any of embodiments 25-48, comprising a preservative or surfactant.
50. The pharmaceutical formulation as recited in embodiment 49, wherein the preservative or surfactant is chosen from ethylenediaminetetraacetic acid (EDTA) or a salt thereof, benzalkonium chloride, and polyvinylpyrrolidone (PVP).
51. The pharmaceutical formulation as recited in any of embodiments 25-50, comprising a viscosity modifier.
52. The pharmaceutical formulation as recited in embodiment 51, wherein the viscosity modifier is a cellulose polymer or polyethylene glycol (PEG).
53. The pharmaceutical formulation as recited in embodiment 52, wherein the viscosity modifier is chosen from hydroxyethylcellulose, methyl cellulose, hypromellose, and PEG-1000.
54. A nasal irrigation fluid comprising
   i. the pharmaceutical formulation as recited in any of embodiments 25-53; and
   ii. a measured volume of distilled water.
55. The nasal irrigation fluid as recited in embodiment 54, wherein the measured volume of distilled water is about 20 to about 400 mL.
56. The nasal irrigation fluid as recited in embodiment 55, wherein the volume is about 100 to about 200 mL.
57. The nasal irrigation fluid as recited in embodiment 56, wherein the volume is about 100 to about 150 mL.
58. The nasal irrigation fluid as recited in embodiment 57, wherein the volume is about 120 mL.
59. The nasal irrigation fluid as recited in any of embodiments 1-24 and 54-58, wherein all excipients, are soluble in the aqueous suspension of cephalosporin antibiotic, cefuroxime or cefuroxime axetil.
60. A sachet for the preparation of a nasal irrigation fluid, comprising:
   i. a disposable container;
   ii. microparticles of a cephalosporin antibiotic having a diameter between about 0.1 and about 10 µm;
   iii. sodium chloride;
   iv. at least one buffering agent;
   v. optionally, at least one preservative or surfactant;
   vi. optionally, a flow agent;
   vii. optionally, a molecular inclusion agent;
   viii. optionally, a viscosity modifier;
   ix. optionally, a suspending agent; and
   x. an amount of an acid or base sufficient to achieve a pH of between about 3 and about 8 when prepared as a nasal irrigation fluid.
61. The sachet as recited in embodiment 60, comprising:
   i. microparticles of a cephalosporin antibiotic having a diameter between about 0.1 and about 10 µm;
   ii. sodium chloride;
   iii. at least one buffering agent;
   iv. a preservative or surfactant; and
   v. a viscosity modifier.
62. The sachet as recited in embodiment 61, comprising:
   i. about 10%-about 50% microparticles of a cephalosporin antibiotic having a diameter between about 0.1 µm and about 10 µm;
   ii. about 25%-about 90% sodium chloride;
   iii. at least one buffering agent, the total amount of buffering agent amounting to about 0.1%-about 2%;
   iv. about 0.005% to about 0.05% of a surfactant; and
   v. about 0.1% to about 1% of a viscosity modifier.
63. The sachet as recited in embodiment 62, comprising:
   i. about 25% microparticles of a cephalosporin antibiotic having a diameter between about 0.1 µm and about 10 µm;
   ii. about 75% sodium chloride;
   iii. at least one buffering agent, the total amount of buffering agent amounting to about 0.4%-about 0.5%;
   iv. about 0.01% to about 0.05% of a surfactant; and
   v. about 0.5% of a viscosity modifier.
64. The sachet as recited in embodiment 63, wherein the buffering agents are a first buffering agent that is an acid, and a second buffering agent that is a salt of the acid.
65. The sachet as recited in embodiment 64, wherein the formulation comprises about 0.2% of the first buffering agent that is an acid, and about 0.28% of the second buffering agent that is a salt of the acid.
66. The sachet as recited in any of embodiments 60-65, wherein:
   the first buffering agent is citric acid or a hydrate thereof;
   the first buffering agent is sodium citrate or a hydrate thereof;
   the surfactant is chosen from polyvinylpyrrolidone (PVP) and disodium ethylenediaminetetraacetic acid (EDTA); and
   the viscosity modifier is polyethylene glycol (PEG) 1000.
67. The sachet as recited in embodiment 66, wherein the surfactant is PVP in an amount of about 0.1%.
68. The sachet as recited in embodiment 67, wherein the surfactant is disodium EDTA in an amount of about 0.5%.
69. The sachet as recited in any of embodiments 60-68, wherein the microparticles of a cephalosporin antibiotic have a diameter between about 1 and about 5 µm.
70. The sachet as recited in embodiment 69, wherein the microparticles of a cephalosporin antibiotic are micronized.
71. The sachet as recited in any of embodiments 60-70, wherein at least 90% of the microparticles have a diameter of less than about 7 µm.
72. The sachet as recited in embodiment 71, wherein at least 90% of the microparticles have a diameter of between about 0.1 µm and about 7 µm.
73. The sachet as recited in embodiment 72, wherein at least 90% of the microparticles of a cephalosporin antibiotic have a diameter between about 0.75 µm and about 5 µm.
74. The sachet as recited in embodiment 73, wherein the microparticles of a cephalosporin antibiotic have the following size distribution:
   10% of microparticles have a diameter of ≤0.75 µm;
   50% of microparticles have a diameter of ≤4.0 µm; and
   90% of microparticles have a diameter of ≤5.0 µm.
75. The sachet as recited in any of embodiments 60-74, wherein the cephalosporin antibiotic agent is cefuroxime.
76. The sachet as recited in embodiment 75, wherein the cephalosporin antibiotic agent is cefuroxime axetil.
77. The sachet as recited in embodiment 76, wherein cefuroxime axetil is present in a dosage of about 50 to about 400 mg.
78. The sachet as recited in embodiment 76, wherein cefuroxime axetil is present in a dosage of about 250 mg.
79. The sachet as recited in embodiment 76, wherein cefuroxime axetil is present in a dosage of about 125 mg.
80. The sachet as recited in any of embodiments 60-79, wherein the buffering agent is a weak acid or base.
81. The sachet as recited in any of embodiments 60-80, wherein the buffering agent maintains the pH of the formulation in the range of about 7.1 and about 7.4

82. The sachet as recited in any of embodiments 60-81, wherein the buffering agent(s) are chosen from sodium bicarbonate, sodium citrate, and citric acid.
83. The sachet as recited in embodiment 82, wherein the buffering agents are sodium citrate and citric acid.
84. The sachet as recited in any of embodiments 60-83, wherein the sachet comprises one or more preservatives or surfactants.
85. The sachet as recited in embodiment 84, wherein the preservative or surfactant is chosen from ethylenediaminetetraacetic acid (EDTA) or a salt thereof, benzalkonium chloride, and polyvinylpyrrolidone (PVP).
86. The sachet as recited in any of embodiments 60-85, which comprises a viscosity modifier.
87. The sachet as recited in embodiment 86 wherein the viscosity modifier is a cellulose polymer or polyethylene glycol (PEG).
88. The sachet as recited in embodiment 87, wherein the viscosity modifier is chosen from hydroxyethylcellulose, methyl cellulose, hypromellose, and PEG-1000.
89. A method for the treatment of sinusitis or a related condition, comprising administering to a sinus of a patient in need thereof a nasal irrigation fluid comprising a suspension of a therapeutically effective amount of a cephalosporin antibiotic.
90. The method as recited embodiment 89, wherein the condition is chosen from acute maxillary sinusitis, acute frontal sinusitis, and acute exacerbation of chronic sinusitis.
91. The method as recited in embodiment 89, wherein the sinusitis is chronic.
92. The method as recited in any of embodiments 89-91, wherein the sinus cavity is a deep sinus cavity.
93. The method as recited in any of embodiments 89-91, wherein the sinus(es) is/are chosen from a frontal sinus, maxillary sinus, turbinates, ethmoids, and sphenoids.
94. The method as recited in embodiment 93, wherein the sinus cavity is the maxillary sinus.
95. The method as recited in any of embodiments 89-94, wherein the microparticles of a cephalosporin antibiotic are micronized.
96. The method as recited in any of embodiments 89-94, wherein at least 90% of the microparticles have a diameter of less than about 7 µm.
97. The method as recited in embodiment 96, wherein at least 90% of the microparticles have a diameter of between about 0.1 µm and about 7 µm.
98. The method as recited in embodiment 97, wherein at least 90% of the microparticles of a cephalosporin antibiotic have a diameter between about 0.75 µm and about 5 µm.
99. The method as recited in embodiment 98, wherein the microparticles of a cephalosporin antibiotic have the following size distribution:
   10% of microparticles have a diameter of ≤0.75 µm;
   50% of microparticles have a diameter of ≤4.0 µm; and
   90% of microparticles have a diameter of ≤5.0 µm.
100. The method as recited in any of embodiments 89-99, wherein the cephalosporin antibiotic is cefuroxime.
101. The method as recited in embodiment 100, wherein the cephalosporin antibiotic is cefuroxime axetil.
102. The method as recited in any of embodiments 89-101, wherein cefuroxime axetil is present in a dosage of about 50 to about 400 mg.
103. The method as recited in embodiment 102, wherein cefuroxime axetil is present in a dosage of about 250 mg.
104. The method as recited in embodiment 102, wherein cefuroxime axetil is present in a dosage of about 125 mg.
105. The method as recited in any of embodiments 89-104, wherein the volume of the nasal irrigation fluid per administration is about 100 to about 200 mL.
106. The method as recited in embodiment 105, wherein the volume of the nasal irrigation fluid per administration is about 100 to about 150 mL.
107. The method as recited in embodiment 106, wherein the cefuroxime axetil is present in the nasal irrigation fluid at a concentration of about 125 mg per 120 ml.
108. The method as recited in any of embodiments 89-107, wherein the nasal irrigation fluid is administered to each nostril, twice a day.
109. The method as recited in embodiment 108, wherein administration of the nasal irrigation fluid is performed twice a day daily for 1 to 30 days.
110. The method as recited in embodiment 108, wherein administration of the nasal irrigation fluid is performed twice a day daily for 7 days.
111. The method as recited in embodiment 108, wherein administration of the nasal irrigation fluid is performed twice a day daily for 10-14 days.
112. The method as recited in embodiment 108, wherein the dosage comprises 125 mg of cefuroxime axetil in 120 mL of nasal irrigation fluid, delivered per nostril, twice a day.
113. The method as recited in any of embodiments 89-112, wherein the nasal irrigation fluid is the nasal irrigation fluid as recited in any of embodiments 1-24 and 54-59.
114. The method as recited in any of embodiments 89-112, comprising the steps of:
   i. preparing a nasal irrigation fluid by combining a measured volume of distilled water with a weighed amount (a dose) of a composition comprising a cephalosporin antibiotic agent, sodium chloride, a buffering agent, an optional viscosity modifier, and suspending the composition in the distilled water; and
   ii. administering the resulting nasal irrigation fluid by dispensing a measured volume of the nasal irrigation fluid into a nasal passage.
115. The method as recited in embodiment 114, wherein the composition is a pharmaceutical formulation as recited in any of embodiments 25-53, or the contents of a sachet as recited in any of embodiments 60-88.
116. The method as recited in embodiment 115, wherein the formed nasal irrigation fluid has an osmolarity of about 225 to 400 mOsm/kg.
117. The method as recited in any of embodiments 89-122, wherein the patient has previously had nasal or sinus surgery.
118. A method for the delivery, to a sinus cavity of a patient with sinusitis or a related condition, of an amount of a cephalosporin antibiotic therapeutically effective to treat the sinusitis or sinus infection, comprising the administration by nasal irrigation of:
   a nasal irrigation fluid as recited in any of embodiments 1-24 and 54-59;
   a nasal irrigation fluid prepared by combining a measured volume of distilled water with the pharmaceutical formulation as recited in any of embodiments 25-53; or the contents of a sachet as recited in any of embodiments 60-88.
119. The method as recited in embodiment 118 wherein the sinus cavity or cavities is/are chosen from a frontal sinus, maxillary sinus, turbinates, ethmoids, and sphenoids.
120. The method as recited in embodiment 118 wherein the sinus cavity is a deep sinus cavity.

121. The method as recited in embodiment 115 wherein the sinus cavity is the maxillary sinus.
122. The method as recited in any of embodiments 118-121, wherein the condition is chosen from acute maxillary sinusitis, acute frontal sinusitis, and acute exacerbation of chronic sinusitis.
123. The method as recited in any of embodiments 118-122, wherein the patient has previously had nasal or sinus surgery.
124. A method of coating one or more of the sinus cavities of a patient with sinusitis or a related condition with an amount of a cephalosporin antibiotic therapeutically effective to treat the sinusitis or sinus infection, comprising the administration by nasal irrigation of:
   a nasal irrigation fluid as recited in any of embodiments 1-24 and 54-59;
   a nasal irrigation fluid prepared by combining a measured volume of distilled water with the pharmaceutical formulation as recited in any of embodiments 25-53; or
   the contents of a sachet as recited in any of embodiments 60-88.
125. The method as recited in embodiment 124, wherein the sinus cavity or cavities is/are chosen from a frontal sinus, maxillary sinus, turbinates, ethmoids, and sphenoids.
126. The method as recited in embodiment 124, wherein the sinus cavity is a deep sinus cavity.
127. The method as recited in embodiment 124, wherein the sinus cavity is the maxillary sinus.
128. The method as recited in embodiment 124, wherein the condition is chosen from acute maxillary sinusitis, acute frontal sinusitis, and acute exacerbation of chronic sinusitis.
129. A method of disruption and/or penetration of a bacterial biofilm in a sinus of, and treatment of sinusitis or a related condition in, a patient in need thereof, comprising administering to a sinus of a patient in need thereof either:
   a nasal irrigation fluid as recited in any of embodiments 1-24 and 54-59; or a nasal irrigation fluid prepared by combining a measured volume of distilled water with the pharmaceutical formulation as recited in any of embodiments 25-53, or the contents of a sachet as recited in any of embodiments 60-88.
130. A method of disruption and/or penetration of a bacterial biofilm in a sinus of a patient with sinusitis or a related condition, comprising administering to a sinus of a patient in need thereof either:
   a nasal irrigation fluid as recited in any of embodiments 1-24 and 54-59; or
   a nasal irrigation fluid prepared by combining a measured volume of distilled water with the pharmaceutical formulation as recited in any of embodiments 25-53, or the contents of a sachet as recited in any of embodiments 60-88.
131. The nasal irrigation fluid as recited in any of embodiments 1-24 and 54-59, the pharmaceutical formulation as recited in any of embodiments 25-53, or the sachet as recited in any of embodiments 60-88, for the treatment of sinusitis or a related condition.
132. The nasal irrigation fluid as recited in any of embodiments 1-24 and 54-59, the pharmaceutical formulation as recited in any of embodiments 25-53, or the sachet as recited in any of embodiments 60-88, for the treatment of a condition chosen from acute maxillary sinusitis, acute frontal sinusitis, and acute exacerbation of chronic sinusitis.
133. A nasal irrigation device comprising a squeeze bottle suitable for nasal irrigation; and either:
   a nasal irrigation fluid as recited in any of embodiments 1-24 and 54-59;
   a nasal irrigation fluid prepared by combining a measured volume of distilled water with the pharmaceutical formulation as recited in any of embodiments 25-53; or
   the contents of a sachet as recited in any of embodiments 60-88.
134. A kit comprising:
   i. a squeeze bottle suitable for nasal irrigation;
   ii. a nasal irrigation fluid as recited in any of embodiments 1-24 and 54-59, a pharmaceutical formulation as recited in any of embodiments 25-53, or a sachet as recited in any of embodiments 60-88; and
   iii. instructions for preparing a nasal irrigation fluid by combining a measured volume of distilled water with the pharmaceutical formulation as recited in any of embodiments 25-53 or the contents of a sachet as recited in any of embodiments 60-88; and
   iv. instructions for administering the nasal irrigation fluid to a sinus cavity.

The detailed description set-forth above is provided to aid those skilled in the art in practicing the present disclosure. However, the disclosure described and claimed herein is not to be limited in scope by the specific embodiments herein disclosed because these embodiments are intended as illustration of several aspects of the disclosure. Any equivalent embodiments are intended to be within the scope of this disclosure. Indeed, various modifications of the disclosure in addition to those shown and described herein will become apparent to those skilled in the art from the foregoing description, which do not depart from the spirit or scope of the present inventive discovery. Such modifications are also intended to fall within the scope of the appended claims.

We claim:

1. A pharmaceutical formulation in liquid suspension form for nasal irrigation, comprising:
   i about 10%-about 50% microparticles consisting of a cephalosporin antibiotic having a diameter less than about 7 μm;
   ii. about 25%-about 90% sodium chloride in water in which the microparticles are suspended;
   iii. at least one buffering agent selected from the group consisting of citric acid monohydrate and sodium citrate dihydrate, the total amount of buffering agent amounting to about 0.1%-about 2%;
   iv. about 0.005% to about 0.5% of a surfactant selected from the group consisting of polyvinylpyrrolidone and di sodium EDTA;
   v. about 0.01% to about 1% of (a) a viscosity modifier comprising polyethylene glycol, or (b) a suspending agent comprising magnesium stearate; and
   vi. an amount of an acid or base sufficient to achieve a pH of between about 3 and about 8 in the liquid suspension;
   wherein a viscosity of the liquid suspension is less than 1.0 mPa·s.

2. The pharmaceutical formulation as recited in claim 1, comprising:
   i. about 10%-about 50% microparticles consisting of a cephalosporin antibiotic having a diameter less than about 7 μm;
   ii. about 25%-about 90% sodium chloride in water in which the microparticles are suspended;
   iii. at least one buffering agent selected from the group consisting of citric acid monohydrate and sodium citrate dihydrate, the total amount of buffering agent amounting to about 0.1%-about 2%;
iv. about 0.005% to about 0.5% of surfactant selected from the group consisting of polyvinylpyrrolidone and disodium EDTA; and
v. about 0.01% to about 1% of a viscosity modifier comprising polyethylene glycol.

3. The pharmaceutical formulation as recited in claim 2, comprising:
i. about 25% microparticles consisting of a cephalosporin antibiotic having a diameter less than about 7 μm;
ii. about 74% sodium chloride in water in which the microparticles are suspended;
iii. at least one buffering agent selected from the group consisting of citric acid monohydrate and sodium citrate dihydrate, the total amount of buffering agent amounting to about 0.4% about 0.5%;
iv. about 0.01% to about 0.05% of a surfactant selected from the group consisting of polyvinylpyrrolidone and disodium EDTA; and
v. about 0.5% of a viscosity modifier comprising polyethylene glycol.

4. The pharmaceutical formulation as recited in claim 3, wherein the formulation comprises about 0.2% of citric acid monohydrate, and about 0.28% of sodium citrate dehydrate.

5. The pharmaceutical formulation as recited in claim 4, wherein the surfactant is polyvinylpyrrolidone in an amount of about 0.01%.

6. The pharmaceutical formulation as recited in claim 4, wherein the surfactant is disodium EDTA in an amount of about 0.05%.

7. The pharmaceutical formulation as recited in claim 1, wherein the particles of a cephalosporin antibiotic are micronized.

8. The pharmaceutical formulation as recited in claim 1, wherein at least 90% of the microparticles of a cephalosporin antibiotic have a diameter between about 0.75 μm and about 5 μm.

9. The pharmaceutical formulation as recited in claim 1, wherein the cephalosporin antibiotic is cefuroxime.

10. The pharmaceutical formulation as recited in claim 9, wherein the cephalosporin antibiotic is cefuroxime axetil.

11. The pharmaceutical formulation as recited in claim 10, wherein cefuroxime axetil is present in a dosage of about 50 mg to about 400 mg.

12. The pharmaceutical formulation as recited in claim 11, wherein cefuroxime axetil is present in a dosage of about 250 mg.

13. The pharmaceutical formulation as recited in claim 11, wherein cefuroxime axetil is present in a dosage of about 125 mg.

14. The pharmaceutical formulation as recited in claim 1, wherein the buffering agent maintains the pH of the formulation in the range of about 7.0 and about 7.4.

* * * * *